United States Patent
Pettit et al.

(10) Patent No.: US 11,548,889 B2
(45) Date of Patent: Jan. 10, 2023

(54) EMETINE AURISTATIN COMPOUNDS

(71) Applicant: Arizona Board of Regents on behalf of Arizona State University, Scottsdale, AZ (US)

(72) Inventors: George R. Pettit, Paradise Valley, AZ (US); Noeleen Melody, Mesa, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 190 days.

(21) Appl. No.: 17/062,295

(22) Filed: Oct. 2, 2020

(65) Prior Publication Data

US 2021/0101900 A1  Apr. 8, 2021

Related U.S. Application Data

(60) Provisional application No. 62/909,586, filed on Oct. 2, 2019.

(51) Int. Cl.
| | | |
|---|---|---|
| *C07D 471/04* | (2006.01) | |
| *A61P 35/04* | (2006.01) | |
| *A61K 45/06* | (2006.01) | |

(52) U.S. Cl.
CPC .......... *C07D 471/04* (2013.01); *A61P 35/04* (2018.01); *A61K 45/06* (2013.01)

(58) Field of Classification Search
CPC ........ C07D 471/04; A61P 35/04; A61K 45/06
USPC .......................................................... 514/294
See application file for complete search history.

(56) References Cited

PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*

* cited by examiner

*Primary Examiner* — Kristin A Vajda
(74) *Attorney, Agent, or Firm* — Riverside Law LLP

(57) ABSTRACT

The present disclosure relates to Emetine Auristatin compounds, pharmaceutical compositions and kits comprising such compounds, and methods for using such compounds or pharmaceutical compositions.

22 Claims, No Drawings

EMETINE AURISTATIN COMPOUNDS

CROSS-REFERENCE

This application claims the benefit of U.S. Provisional Application No. 62/909,586, filed Oct. 2, 2019, which is incorporated herein by reference in its entirety.

BACKGROUND OF THE INVENTION

Emetine is a tetrahydroisoquinoline alkaloid found predominantly in the roots of the plant species *Carapichea ipecacuanha* (Brot.) L. Andersson, otherwise known as *Psychotria ipecacuanha* (Brot.) Stokes, and named for its emetic properties.[1a-c] Earlier it was also used as an amoebicidal agent until the mid-20th century.[2] More recently it was found to inhibit protein, DNA, and RNA synthesis and therefore non-specifically cytotoxic to all cells with activity in the NCI 60 Cancer cell screen ($GI_{50}$ of 27 nM).[3a-c]

Emetine was found to inhibit Nuclear Factor-kappa B (NF-kB) signaling; dysregulation of this signaling pathway is connected to diseases including cancer.[4] In addition, emetine promotes apoptosis in malignant cells by upregulation of the Bcl-xS splicing variant.[4a] Furthermore it has been shown that both the (R) configuration at C-1' and the methoxy group at C-7' are essential for the biological activity of emetine and that alkylation of the secondary amine at position N-2' causes loss of activity.[5a-c] In more targeted therapy studies, derivatives with thiourea, urea, sulfonamide, dithiocarbamate, carbamates, amides and peptides at the N-2' position have been investigated as prodrugs to be activated in either a lower pH environment of a tumor, proteolysis by proteases fibroblast activation protein (FAP), or the Prostate-Specific antigen (PSA). These derivatives were found to generally reduce emetine's biological activity, with the dithiocarbamates being further evaluated as less toxic analogues of emetine and the peptides as prodrugs for prostate cancer treatments.[6a-e]

The present inventors investigated the construction of peptides from the N-2' position of emetine.[7] The biological activity of proline-emetine analogues has been reported and found to be 150-200 fold less cytotoxic than emetine.[6d]

Citation of any reference in this section is not to be construed as an admission that such reference is prior art to the present disclosure.

BRIEF SUMMARY OF THE INVENTION

The present disclosure relates to emetine compounds, pharmaceutical compositions and kits comprising such compounds, and methods for using such compounds or pharmaceutical compositions. Surprisingly, the compounds have, or are believed to have, biological activity similar to that of emetine.

In a first embodiment, the present disclosure provides a compound of formula (I):

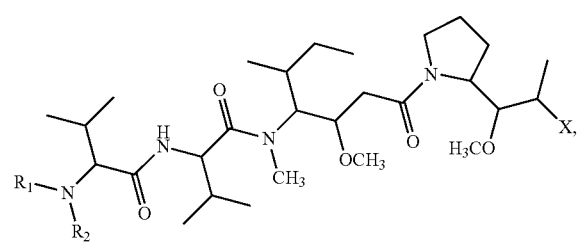

(I)

or a pharmaceutically acceptable salt thereof, wherein $R_1$ is selected from H, ($C_1$-$C_6$) alkyl, ($C_2$-$C_6$) alkenyl, ($C_2$-$C_6$) alkynyl, a Protecting Group or a Linker Unit;

$R_2$ is selected from H, ($C_1$-$C_6$) alkyl, ($C_2$-$C_6$) alkenyl or ($C_2$-$C_6$) alkynyl;

X is —C(O)$R_4$, —C(O)NH—($C_{1-6}$ alkyl)-C(=O)—$R_4$, —C(O)NH—($C_{1-6}$ alkyl)-$R_4$, —($C_{1-6}$ alkyl)-C(=O)—$R_4$, —($C_{1-6}$ alkyl)-$R_4$, —($C_{1-6}$ alkyl)S(O)—$R_4$, —($C_{1-6}$ alkyl)-OS(O)—$R_4$, —($C_{1-6}$ alkyl)-OS(O)O—$R_4$, —S(O)—$R_4$, —OS(O)—$R_4$, or —OS(O)—$R_4$;

$R_4$ is

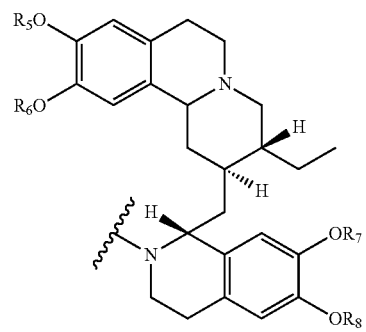

$R_5$, $R_6$, $R_7$ and $R_8$ are independently selected from the group consisting of H, ($C_1$-$C_6$) alkyl, ($C_2$-$C_6$) alkenyl, ($C_2$-$C_6$) alkynyl, a Protecting Group and a Linker Unit.

In a second embodiment, the present disclosure provides a compound of formula (Ia):

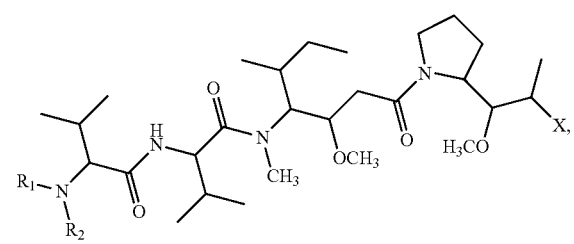

(Ia)

or a pharmaceutically acceptable salt thereof, wherein $R_1$ is selected from H, ($C_1$-$C_6$) alkyl, ($C_2$-$C_6$) alkenyl, ($C_2$-$C_6$) alkynyl, a Protecting Group or a Linker Unit;

$R_2$ is selected from H, ($C_1$-$C_6$) alkyl, ($C_2$-$C_6$) alkenyl or ($C_2$-$C_6$) alkynyl;

X is —C(O)$R_4$, —C(O)NH—($C_{1-6}$ alkyl)-C(=O)—$R_4$, —C(O)NH—($C_{1-6}$ alkyl)-$R_4$, —($C_{1-6}$ alkyl)-C(=O)—$R_4$, —($C_{1-6}$ alkyl)-$R_4$, —($C_{1-6}$ alkyl)S(O)—$R_4$, —($C_{1-6}$ alkyl)-OS(O)—$R_4$, —($C_{1-6}$ alkyl)-OS(O)O—$R_4$, —S(O)—$R_4$, —OS(O)—$R_4$, or —OS(O)O—$R_4$;

$R_4$ is

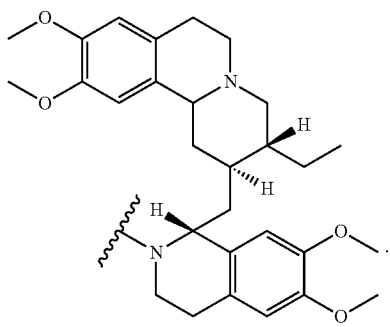

In a third embodiment, the present disclosure provides a compound of formula (Ib):

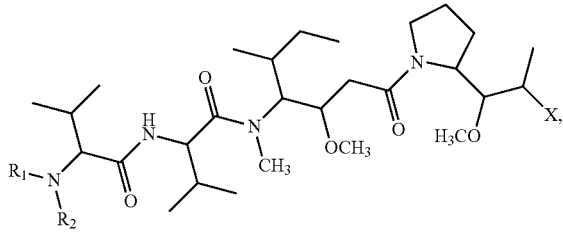

or a pharmaceutically acceptable salt thereof, wherein $R_1$ is selected from H, $(C_1\text{-}C_6)$ alkyl, $(C_2\text{-}C_6)$ alkenyl, $(C_2\text{-}C_6)$ alkynyl, a Protecting Group or a Linker Unit;

$R_2$ is selected from H, $(C_1\text{-}C_6)$ alkyl, $(C_2\text{-}C_6)$ alkenyl or $(C_2\text{-}C_6)$ alkynyl;

X is —C(O)$R_4$, —C(O)NH—$(C_{1\text{-}6}$ alkyl)-C(=O)—$R_4$, or —C(O)NH—$(C_{1\text{-}6}$ alkyl)-$R_4$;

$R_4$ is

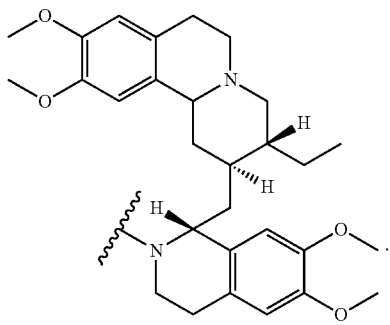

The compounds of this disclosure have or are believed to have biological activity similar to that of emetine. In particular, compounds of formula (I) exhibit cancer cell growth inhibitory activities similar to that of emetine. See Example 4. The activity of the compounds of formula (I) is surprising as the activity of emetine is usually lost or greatly reduced when substituted at the N2' position.

DETAILED DESCRIPTION OF THE INVENTION

The invention includes the following:
(1.) A compound of formula (I):

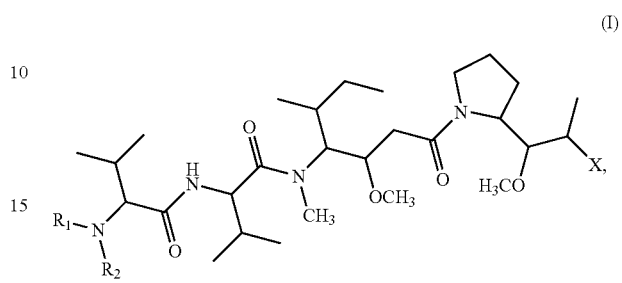

or a pharmaceutically acceptable salt thereof, wherein
$R_1$ is selected from H, $(C_1\text{-}C_6)$ alkyl, $(C_2\text{-}C_6)$ alkenyl, $(C_2\text{-}C_6)$ alkynyl, a Protecting Group or a Linker Unit;

$R_2$ is selected from H, $(C_1\text{-}C_6)$ alkyl, $(C_2\text{-}C_6)$ alkenyl or $(C_2\text{-}C_6)$ alkynyl;

X is —C(O)$R_4$, —C(O)NH—$(C_{1\text{-}6}$ alkyl)-C(=O)—$R_4$, —C(O)NH—$(C_{1\text{-}6}$ alkyl)-$R_4$, —$(C_{1\text{-}6}$ alkyl)-C(=O)—$R_4$, —$(C_{1\text{-}6}$ alkyl)-$R_4$, alkyl)S(O)—$R_4$, alkyl)-OS(O)—$R_4$, alkyl)-OS(O)O—$R_4$, —S(O)—$R_4$, —OS(O)—$R_4$, or —OS(O)O—$R_4$;

$R_4$ is

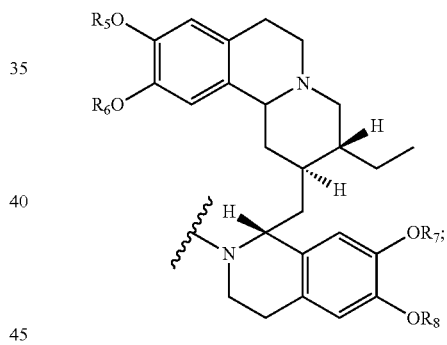

and
$R_5$, $R_6$, $R_7$ and $R_8$ are independently selected from the group consisting of H, $(C_1\text{-}C_6)$ alkyl, $(C_2\text{-}C_6)$ alkenyl, $(C_2\text{-}C_6)$ alkynyl, a Protecting Group and a Linker Unit.

(2.) The compound of the above (1) or a pharmaceutically acceptable salt thereof, wherein the compound has formula (Ia):

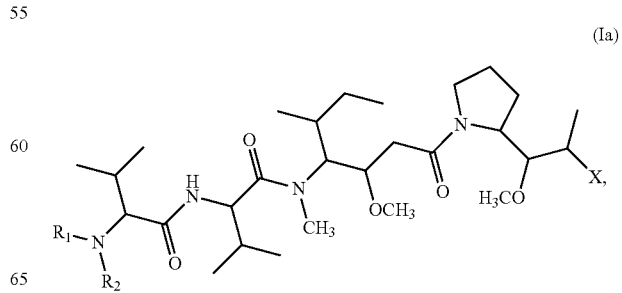

and R₄ is

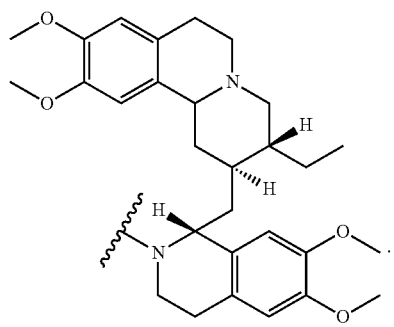

(3.) The compound of the above (1) or a pharmaceutically acceptable salt thereof, wherein the compound has formula (Ib):

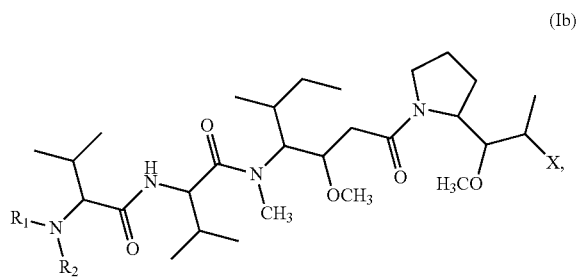

X is —C(O)R₄, —C(O)NH—(C₁₋₆ alkyl)-C(=O)—R₄, or —C(O)NH—(C₁₋₆ alkyl)-R₄; and
R₄ is

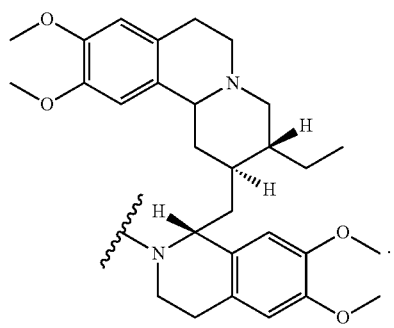

(4.) The compound of any one of the above (1.) to (3.), wherein $R_1$ is H, ($C_1$-$C_6$) alkyl, or a Linker Unit.

(5.) The compound of any one of the above (1.) to (3.), wherein $R_1$ is H.

(6.) The compound of any one of the above (1.) to (3.), wherein $R_1$ is ($C_1$-$C_6$) alkyl.

(7.) The compound of any one of the above (1.) to (3.), wherein $R_1$ is methyl.

(8.) The compound of any one of the above (1.) to (3.), wherein $R_1$ is a Linker Unit.

(9.) The compound of any one of the above (1.) to (8.), wherein $R_2$ is H or ($C_1$-$C_6$) alkyl.

(10.) The compound of any one of the above (1.) to (8.), wherein $R_2$ is H.

(11.) The compound of any one of the above (1.) to (8.), wherein $R_2$ is ($C_1$-$C_6$) alkyl.

(12.) The compound of any one of the above (1.) to (8.), wherein $R_2$ is methyl.

(13.) The compound of any one of the above (1.) to (12.), wherein X is —C(O)R₄, —(C₁₋₆ alkyl)-R₄, —(C₁₋₆ alkyl)S(O)—R₄, —(C₁₋₆ alkyl)-OS(O)—R₄, —(C₁₋₆ alkyl)-OS(O)O—R₄, —OS(O)—R₄, or —OS(O)O—R₄.

(14.) The compound of any one of the above (1.) to (12.), wherein X is —C(O)R₄, —(C₁₋₆ alkyl)-R₄, —(C₁₋₆ alkyl)S(O)—R₄, —OS(O)—R₄, or —OS(O)—R₄;

(15.) The compound of any one of the above (1.) to (12.), wherein X is —C(O)R₄.

(16.) The compound of the above (1.), wherein $R_5$, $R_6$, $R_7$ and $R_8$ are independently H or ($C_1$-$C_6$) alkyl.

(17.) The compound of any of the above (1.) to (16.), wherein the Linker Unit comprises a cleavable linker.

(18.) The compound of the above (17.), wherein the cleavable linker is cleavable by a method selected from the group consisting of glycosidase-induced cleavage, acid-induced cleavage, light-induced cleavage, peptidase-induced cleavage, esterase-induced cleavage, and disulfide bond cleavage.

(19.) The compound of the above (17.), wherein the cleavable linker comprises a glycosidic bond, a hydrazone, a cathepsin-B-cleavable peptide, a disulfide or an ester bond.

(20.) The compound of any one of the above (1.) to (16.), wherein the Linker Unit has formula:

$A_aW_wY_y$, wherein $A_a$ is maleimidocaproyl, $W_w$ is Valine-Citrulline and $Y_y$ is p-aminobenzyloxycarbonyl.

(21.) The compound of the above (18.), wherein the cleavable linker comprises glucuronide.

(22.) The compound of any of the above (1.) to (16.) or (20.), wherein the Linker Unit comprises a monoclonal antibody.

(23.) A compound selected from the group consisting of:

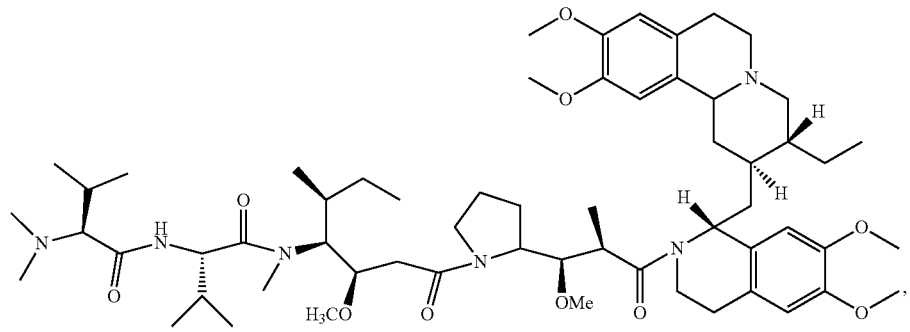

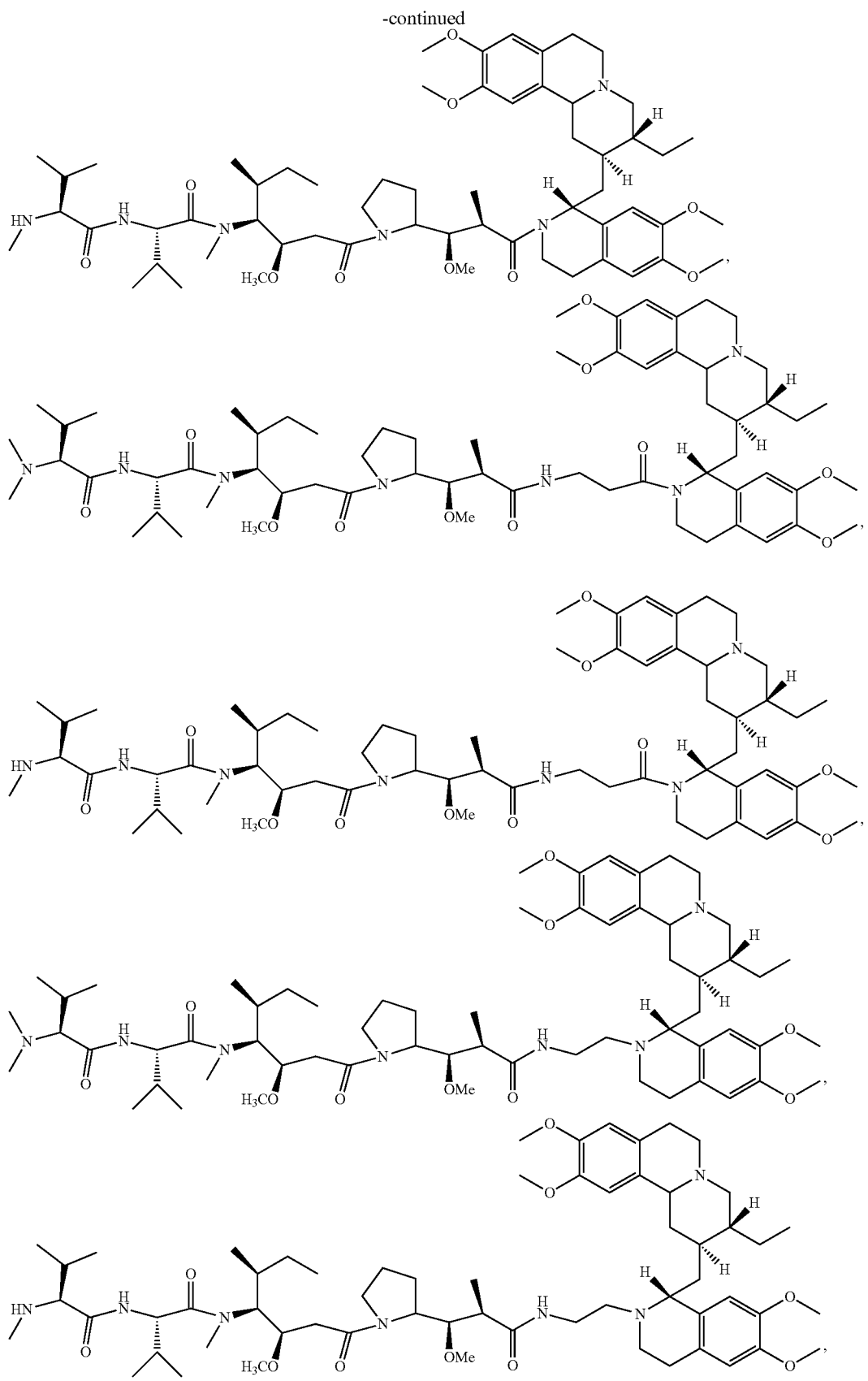
and pharmaceutically acceptable salts thereof.

(24.) A compound, which is

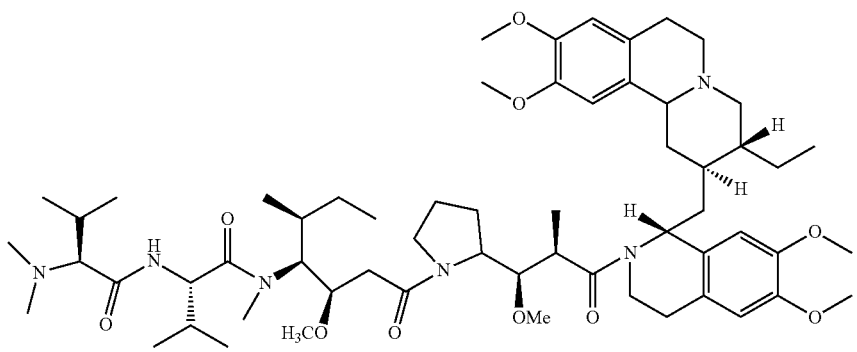

or a pharmaceutically acceptable salt thereof.

(25.) A pharmaceutical composition comprising a compound of the above (1.) to (24.) or pharmaceutically acceptable salts thereof and a pharmaceutically acceptable carrier.

(26.) A pharmaceutical composition comprising a combination of compounds of the above (1.) to (24.) or pharmaceutically acceptable salts thereof and a pharmaceutically acceptable carrier.

(27.) The pharmaceutical composition of the above (25.) or (26.), further comprising a therapeutically effective amount of a second therapeutic agent selected from the group consisting of a tubulin-forming inhibitor, a topoisomerase inhibitor, and a DNA binder.

(28.) A method for killing or inhibiting the proliferation of tumor cells or cancer cells comprising treating the tumor cells or cancer cells with a compound of any of the above (1.) to (24), or a pharmaceutical composition of any one of the above (25.) to (27.), in an amount effective to kill or inhibit the proliferation of the tumor cells or cancer cells.

(29.) A method for treating cancer in a patient in need thereof comprising administering to the patient a compound of any of the above (1.) to (24.), or a pharmaceutical composition of the above (25.), wherein the compound or pharmaceutical composition is administered in an amount effective to treat cancer.

(30.) The method of the above (29.), further comprising administering an effective amount of a second therapeutic agent.

(31.) The method of the above (29.), wherein the cancer is selected from the group consisting of breast cancer, ovarian cancer, stomach cancer, endometrial cancer, salivary gland cancer, lung cancer, kidney cancer, colon cancer, colorectal cancer, thyroid cancer, pancreatic cancer, prostate cancer, bladder cancer and central nervous system cancer.

(32.) The method of the above (29.), wherein the cancer is selected from the group consisting of breast cancer, lung cancer, colon cancer, pancreatic cancer, prostate cancer and central nervous system cancer.

(33.) A method of determining inhibition of cellular proliferation by a compound, comprising contacting cells in a cell culture medium with the compound of any of the above (1.) to (24.) and measuring the cytotoxic activity of the compound, whereby proliferation of the cells is inhibited.

(34.) A method of inhibiting the growth of tumor cells that overexpress a tumor-associated antigen comprising administering to a patient the compound of any of the above (1.) to (24.) conjugated to an antibody that is specific for said tumor-associated antigen, and optionally a second therapeutic agent wherein the compound and the second therapeutic agent are each administered in amounts effective to inhibit the growth of tumor cells in the patient.

(35.) The method of the above (34.), wherein the compound sensitizes the tumor cells to said second therapeutic agent.

(36.) The method of the above (34.), wherein the compound induces cell death.

(37.) The method of the above (34.), wherein the compound induces apoptosis.

(38.) A use of the compound of any of the above (1.) to (24.) in the manufacture of a medicament for treating cancer.

(39.) An article of manufacture comprising the compound of any of the above (1.) to (24.), a container, and a package insert or label indicating that the compound can be used to treat cancer characterized by the overexpression of at least one tumor-associated antigen.

Definitions

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The phrase "pharmaceutically acceptable salt," as used herein, refers to pharmaceutically acceptable organic or inorganic salts of a compound of the disclosure. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The term "pharmaceutically acceptable carrier" refers to a diluent, adjuvant or excipient, with which a compound of the disclosure may be administered. Pharmaceutically acceptable carriers include any and all solvents, diluents, or other liquid vehicles, dispersions or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the disclosure such as by producing any undesirable biological effect or otherwise interacting in a deleterious manner with any other component(s) of the pharmaceutically acceptable composition, its use is contemplated to be within the scope of this disclosure. Examples of pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols, such a propylene glycol or polyethylene glycol; esters, such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "therapeutically effective amount" refers to an amount of a compound of the disclosure or a pharmaceutically acceptable salt thereof effective to treat a cancer in a patient. For purposes of this disclosure, the therapeutically effective amount of the compound may reduce the number of cancer cells; reduce the tumor size; reduce to some extent cancer cell infiltration into peripheral organs, tumor metastasis or tumor growth; and/or relieve to some extent one or more of the symptoms associated with the cancer.

The terms "treat" or "treatment" refer to therapeutic treatment and prophylactic measures to obtain a beneficial or desired result. For purposes of this disclosure, beneficial or desired results include, but are not limited to, alleviation of symptoms, diminishment of extent of disease, stabilized (i.e., not worsening) state of disease, delay or slowing of disease progression, amelioration or palliation of the disease state, remission (whether partial or total), whether detectable or undetectable and prevention of relapse. "Treatment" can also include prolonging survival as compared to expected survival if not receiving treatment. Those in need of treatment include those already having the condition or disorder as well as those prone to have the condition or disorder.

The terms "cancer" and "cancerous" refer to or describe the physiological condition or disorder in mammals that is typically characterized by unregulated cell growth. A "tumor" comprises one or more cancerous cells.

Exemplary cancers include, but not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, central nervous system cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute non-lymphocytic leukemia, acute undifferentiated leukemia, chronic myelocytic leukemia (CML), chronic lymphocytic leukemia (CLL), hairy cell leukemia, multiple myeloma, Hodgkin's disease, non-Hodgkin's lymphoma, Waldenstrom's macroglobulinemia, heavy chain disease and polycythemia vera.

The term "cytotoxic activity" refers to a cell-killing, a cytostatic or an anti-proliferative effect of a compound of the disclosure. Methods for measuring cytotoxic activity are well-known in the art. Cytotoxic activity may be expressed as the $IC_{50}$ value, which is the concentration (molar or mass) per unit volume at which half the cells survive.

The term "patient," as used herein, includes, but is not limited to, a human, rat, mouse, guinea pig, monkey, pig, goat, cow, horse, dog, cat, bird and fowl. In some embodiments, the patient is a human.

The term "$(C_1-C_6)$ alkyl" refers to saturated linear or branched hydrocarbon structures having 1, 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of "$(C_1-C_6)$ alkyl groups include methyl, ethyl, n-propyl, iso-propyl, n-butyl, tert-butyl, n-pentyl, n-hexyl, and the like.

The term "$(C_1-C_3)$ alkyl" refers to saturated linear or branched hydrocarbon structures having 1, 2 or 3 carbon atoms. When an alkyl residue having a specific number of carbons is named, all geometric isomers having that number of carbons are intended to be encompassed; thus, for example, "propyl" includes n-propyl and iso-propyl. Examples of "($C_1$-$C_3$) alkyl groups include methyl, ethyl, n-propyl and iso-propyl.

The term "($C_2$-$C_6$) alkenyl" refers to a straight-chain or branched unsaturated hydrocarbon radical having 2, 3, 4, 5 or 6 carbon atoms and a double bond in any position, e.g., ethenyl, 1 propenyl, 2 propenyl (allyl), 1-butenyl, 2-butenyl, 3-butenyl, 1-methylethenyl, 1-methyl-1 propenyl, 2 methyl-2-propenyl, 2-methyl-1-propenyl, 1-methyl-2-propenyl, 1-hexenyl, 2-hexenyl, 3-hexenyl, 2-methyl-2-pentenyl, 4-methyl-2-pentenyl, 4-methyl-1-pentenyl, 3-methyl-1-pentenyl, and the like.

The term "($C_2$-$C_6$)alkynyl" refers to a straight chain or branched hydrocarbon having 2, 3, 4, 5 or 6 carbon atoms and including at least one carbon-carbon triple bond. Examples of alkynyl include ethynyl, propynyl, 1-butynyl, 2-butynyl, 1-pentynyl, 2-pentynyl, 1-hexynyl, 2-hexynyl, 3-hexynyl, 4-methyl-2-pentynyl and the like.

The term "Protecting Group" refers to any group that is capable of reversibly protecting another functional group from undergoing an undesired reaction. Suitable oxygen and nitrogen protecting groups, as well as suitable conditions for protection and deprotection are well-known in the art and are described e.g., in T. W. Greene and P. G. M. Wuts, "Protective Groups in Organic Synthesis", Third edition, Wiley, New York 1999, and references cited therein. Representative hydroxy protecting groups include acetates (e.g., pivaloate and benzoate), benzyl ether, p-methoxybenzyl ether, trityl ether, tetrahydropyranyl ether, trialkylsilyl ethers (e.g., trimethylsilyl ether, triethylsilyl ether, triisopropyl silyl ether, t-butyldimethyl silyl ether, triphenylmethyl silyl ether), allyl ethers, methoxymethyl ether, 2-methoxyethoxymethyl ether, methanesulfonate and p-toluenesulfonate. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

The term "Linker Unit" refers to a bifunctional moiety that links or attaches a compound of formula (I) as described herein to another molecule, e.g., an antibody. The Linker Unit can be cleavable or non-cleavable. In embodiments in which the Linker Unit is cleavable, cleavage provides a release of the compound of formula (I). In embodiments in which the Linker Unit is non-cleavable, the molecule remains attached to the compound of formula (I).

The term "antibody" as used herein includes whole antibodies, monoclonal antibodies, polyclonal antibodies, monospecific antibodies, multispecific antibodies (e.g., bispecific antibodies), and antibody fragments that exhibit the desired biological activity. An antibody may be of any type or class (e.g., IgG, IgE, IgM, IgD, and IgA) or subclass (e.g., IgG1, IgG2, IgG3, IgG4, IgA1 and IgA2). The antibody may be derived from any suitable species. In some embodiments, the antibody is of human or murine origin. An antibody may be, for example, human, humanized or chimeric.

The term "monoclonal antibodies" as used herein refers to antibodies produced by a single clone of cells or cell line and comprising identical antibody molecules. The term "polyclonal antibodies" refers to antibodies produced by more than one type of cell or cell line and comprising different antibody molecules.

A compound of the disclosure can contain one, two, or more asymmetric centers and thus can give rise to enantiomers, diastereomers, and other stereoisomeric forms. The disclosure encompasses compounds with all such possible forms, as well as their racemic and resolved forms or any mixture thereof, unless specifically otherwise indicated. When a compound of the disclosure contains an olefinic double bond, a C=N double bond, or any other center of geometric asymmetry, it is intended to include all "geometric isomers", e.g., both Z and E geometric isomers, unless specifically otherwise indicated. All "tautomers", e.g., amine-imine, enamine-enimine, enamine-imine, urea-isourea, ketone-enol, amide-imidic acid, lactam-lactim, are intended to be encompassed by the disclosure as well unless specifically otherwise indicated.

Compounds of Formula (I)

In one embodiment, the present disclosure provides a compound of formula (I),

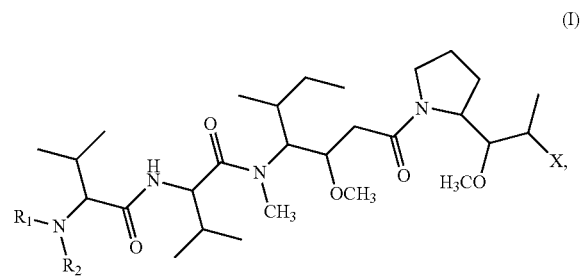

(I)

or a pharmaceutically acceptable salt thereof, wherein $R_1$ is selected from H, ($C_1$-$C_6$) alkyl, ($C_2$-$C_6$) alkenyl, ($C_2$-$C_6$) alkynyl, a Protecting Group or a Linker Unit;

$R_2$ is selected from H, ($C_1$-$C_6$) alkyl, ($C_2$-$C_6$) alkenyl or ($C_2$-$C_6$) alkynyl;

X is —C(O)$R_4$, —C(O)NH—($C_{1-6}$ alkyl)-C(=O)—$R_4$, —C(O)NH—($C_{1-6}$ alkyl)-$R_4$, —($C_{1-6}$ alkyl)-C(=O)—$R_4$, —($C_{1-6}$ alkyl)-$R_4$, —($C_{1-6}$ alkyl)S(O)—$R_4$, —($C_{1-6}$ alkyl)-OS(O)—$R_4$, —($C_{1-6}$ alkyl)-OS(O)O—$R_4$, —S(O)—$R_4$, —OS(O)—$R_4$, or —OS(O)O—$R_4$;

$R_4$ is

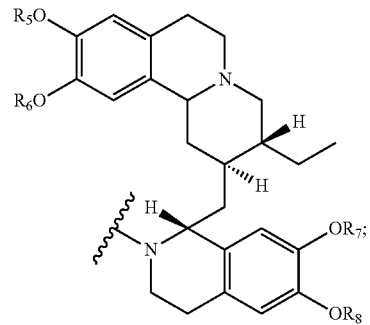

and $R_5$, $R_6$, $R_7$ and $R_8$ are independently selected from the group consisting of H, ($C_1$-$C_6$) alkyl, ($C_2$-$C_6$) alkenyl, ($C_2$-$C_6$) alkynyl, a Protecting Group and a Linker Unit.

In one embodiment, $R_1$ is H, ($C_1$-$C_6$) alkyl or a Linker Unit. In another embodiment, $R_1$ is H or ($C_1$-$C_6$) alkyl. In another embodiment, $R_1$ is H or a Linker Unit. In another embodiment, $R_1$ is ($C_1$-$C_6$) alkyl or a Linker Unit. In another embodiment, $R_1$ is H, methyl or a Linker Unit. In another embodiment, $R_1$ is H or methyl. In another embodiment, $R_1$ is H or a Linker Unit. In another embodiment, $R_1$ is methyl or a Linker Unit. In another embodiment, $R_1$ is H. In another embodiment, $R_1$ is methyl. In another embodiment, $R_1$ is a Linker Unit.

In one embodiment, $R_2$ is H or $(C_1\text{-}C_6)$ alkyl. In another embodiment, $R_2$ is H or methyl. In another embodiment, $R_2$ is H. In another embodiment, $R_2$ is $(C_1\text{-}C_6)$ alkyl. In another embodiment, $R_2$ is methyl.

In one embodiment, X is —C(O)$R_4$, —C(O)NH—$(C_{1-6}$ alkyl)-C(=O)—$R_4$, —C(O)NH—$(C_{1-6}$ alkyl)-$R_4$, —$(C_{1-6}$ alkyl)-C(=O)—$R_4$, alkyl)-$R_4$, alkyl)S(O)—$R_4$, —$(C_{1-6}$ alkyl)-OS(O)—$R_4$, —$(C_{1-6}$ alkyl)-OS(O)O—$R_4$, —S(O)—$R_4$, —OS(O)—$R_4$, or —OS(O)O—$R_4$. In another embodiment, X is —C(O)$R_4$, —$(C_{1-6}$ alkyl)-$R_4$, —$(C_{1-6}$ alkyl)S(O)—$R_4$, alkyl)-OS(O)—$R_4$, —$(C_{1-6}$ alkyl)-OS(O)O—$R_4$, —S(O)—$R_4$, —OS(O)—$R_4$, or —OS(O)O—$R_4$. In another embodiment, X is —C(O)$R_4$, $(C_{1-6}$ alkyl)-$R_4$, —$(C_{1-6}$ alkyl)S(O)—$R_4$, —S(O)—$R_4$, —OS(O)—$R_4$, or —OS(O)O—$R_4$. In another embodiment, X is —C(O)$R_4$ or —C(O)NH—$(C_{1-6}$ alkyl)-C(=O)—$R_4$. In another embodiment, X is —C(O)$R_4$ or —C(O)NH—$(C_{1-6}$ alkyl)-$R_4$. In another embodiment, X is —C(O)$R_4$ or —C(O)C(O)NH—$(C_{1-6}$ alkyl)-C(=O)—$R_4$. In another embodiment, X is —C(O)$R_4$ or —C(O)NH—$(C_2$ alkyl)-$R_4$. In another embodiment, X is —C(O)$R_4$ or —C(O)NH—$(C_2$ alkyl)-C(=O)—$R_4$. In another embodiment, X is —C(O)$R_4$. In another embodiment, X is —C(O)NH—$(C_{1-6}$ alkyl)-C(=O)—$R_4$. In another embodiment, X is —C(O)NH—$(C_2$ alkyl)-C(=O)—$R_4$. In another embodiment, X is —C(O)NH—$(C_{1-6}$ alkyl)-$R_4$. In another embodiment, X is —C(O)NH—$(C_2$ alkyl)-$R_4$.

In one embodiment, $R_5$, $R_6$, $R_7$ and $R_8$ are independently H, $(C_1\text{-}C_6)$ alkyl, a Protecting Group or a Linker Unit. In another embodiment, $R_5$, $R_6$, $R_7$ and $R_8$ are independently H, $(C_1\text{-}C_6)$ alkyl or a Linker Unit. In another embodiment, $R_5$, $R_6$, $R_7$ and $R_8$ are independently H or $(C_1\text{-}C_6)$ alkyl. In another embodiment, $R_5$, $R_6$, $R_7$ and $R_8$ are independently H or methyl. In another embodiment, at least one of $R_5$, $R_6$, $R_7$ and $R_8$ is methyl and the other(s) is H. In another embodiment, one of $R_5$, $R_6$, $R_7$ and $R_8$ is methyl and the others are H. In another embodiment, two of $R_5$, $R_6$, $R_7$ and $R_8$ is methyl and the others are H. In another embodiment, three of $R_5$, $R_6$, $R_7$ and $R_8$ are methyl and the other is H. In another embodiment, each of $R_5$, $R_6$, $R_7$ and $R_8$ is methyl. In another embodiment, each of $R_5$, $R_6$, $R_7$ and $R_8$ is H. In one embodiment, $R_1$ is H, $(C_1\text{-}C_6)$ alkyl or a Linker Unit and $R_2$ is H or $(C_1\text{-}C_6)$ alkyl. In another embodiment, $R_1$ is H or $(C_1\text{-}C_6)$ alkyl and $R_2$ is H or $(C_1\text{-}C_6)$ alkyl. In another embodiment, $R_1$ is H or a Linker Unit and $R_2$ is H or $(C_1\text{-}C_6)$ alkyl. In another embodiment, $R_1$ is $(C_1\text{-}C_6)$ alkyl or a Linker Unit and $R_2$ is H or $(C_1\text{-}C_6)$ alkyl. In another embodiment, $R_1$ is H, methyl or a Linker Unit and $R_2$ is H or $(C_1\text{-}C_6)$ alkyl. In another embodiment, $R_1$ is H or methyl and $R_2$ is H or $(C_1\text{-}C_6)$ alkyl. In another embodiment, $R_1$ is H or a Linker Unit and $R_2$ is H or $(C_1\text{-}C_6)$ alkyl. In another embodiment, $R_1$ is methyl or a Linker Unit and $R_2$ is H or $(C_1\text{-}C_6)$ alkyl. In another embodiment, $R_1$ is H and $R_2$ is H or $(C_1\text{-}C_6)$ alkyl. In another embodiment, $R_1$ is methyl and $R_2$ is H or $(C_1\text{-}C_6)$ alkyl. In another embodiment, $R_1$ is a Linker Unit and $R_2$ is H or $(C_1\text{-}C_6)$ alkyl.

In one embodiment, $R_1$ is H, $(C_1\text{-}C_6)$ alkyl or a Linker Unit and $R_2$ is H or methyl. In another embodiment, $R_1$ is H, $(C_1\text{-}C_6)$ alkyl or a Linker Unit and $R_2$ is H. In another embodiment, $R_1$ is H, $(C_1\text{-}C_6)$ alkyl or a Linker Unit and $R_2$ is $(C_1\text{-}C_6)$ alkyl. In another embodiment, $R_1$ is H, $(C_1\text{-}C_6)$ alkyl or a Linker Unit and $R_2$ is methyl.

In one embodiment, $R_1$ is methyl and $R_2$ is methyl. In another embodiment, $R_1$ is H and $R_2$ is methyl. In another embodiment, $R_1$ is H and $R_2$ is H. In another embodiment, $R_1$ is a Linker Unit and $R_2$ is methyl. In another embodiment, $R_1$ is a Linker Unit and $R_2$ is H.

In one embodiment, the compound of formula (I) may be conjugated to an antibody. The antibody may be conjugated to the compound of the formula (I) through the N-terminus or the C-terminus. In one embodiment, the antibody is conjugated to the antibody at the N-terminus. In another embodiment, the antibody is conjugated to the antibody at the C-terminus. In one embodiment, the compound of formula (I) is conjugated directly to an antibody. In another embodiment, the compound of formula (I) is conjugated to an antibody through a Linker Unit. The Linker Unit can operate to provide a suitable release of the compound of formula (I). The preparation of antibody drug conjugates is known to those of skill in the art.

In embodiments in which the compound of formula (I) is conjugated to an antibody through a Linker Unit, the Linker Unit may comprise a cleavable linker in one embodiment and a non-cleavable linker in another embodiment.

In embodiments in which $R_1$ comprises a cleavable linker, the cleavable linker may be cleaved by methods known in the art. In one embodiment, the cleavable linker may be cleaved by a method selected from the group consisting of glycosidase-induced cleavage, acid-induced cleavage, light-induced cleavage, peptidase-induced cleavage, esterase-induced cleavage, and disulfide bond cleavage. In one embodiment, the cleavage method is selected from the group consisting of glycosidase-induced cleavage, acid-induced cleavage, peptidase-induced cleavage, esterase-induced cleavage, and disulfide bond cleavage. In another embodiment, the cleavage method is selected from the group consisting of glycosidase-induced cleavage, peptidase-induced cleavage, and esterase-induced cleavage. In another embodiment, the cleavage method is selected from glycosidase-induced cleavage or peptidase-induced cleavage. In another embodiment, the cleavage method is selected from glycosidase-induced cleavage or esterase-induced cleavage. In another embodiment, the cleavage method is selected from peptidase-induced cleavage or esterase-induced cleavage.

In embodiments in which $R_1$ comprises a cleavable linker, the cleavable linker may comprise a glycosidic bond, a hydrazone, a cathepsin-B-cleavable peptide, a disulfide or an ester bond. In one embodiment, the cleavable linker comprises a glycosidic bond, a hydrazone, a cathepsin-B-cleavable peptide, or an ester bond. In one embodiment, the cleavable linker comprises a glycosidic bond, a hydrazone, or a cathepsin-B-cleavable peptide. In one embodiment, the cleavable linker comprises a glycosidic bond, a hydrazone, or an ester bond. In one embodiment, the cleavable linker comprises a glycosidic bond, a cathepsin-B-cleavable peptide, or an ester bond. In one embodiment, the cleavable linker comprises a hydrazone, a cathepsin-B-cleavable peptide, or an ester bond.

In one embodiment, the cleavable linker comprises a glycosidic bond. In one embodiment, the cleavable linker comprises glucuronide.

The compounds of the disclosure may be conjugated to any antibody, e.g., an antibody that binds to a tumor associated antigen. In one embodiment, the antibody used in the antibody drug conjugate of the disclosure is a monoclonal antibody. The antibody can be a chimeric antibody, a humanized antibody or an antibody fragment. In another embodiment, the antibody used in the antibody drug conjugate of the disclosure binds at least one of CD19, CD20, CD30, CD33, CD70, BCMA, Glypican-3, Liv-1 and Lewis Y antigens.

In one embodiment, the Linker Unit is a bifunctional moiety that can be used to conjugate a compound of formula (I) to an antibody. Such bifunctional moieties are known in the art and include, but are not limited to, alkyldiyl, an aryldiyl, a heteroaryldiyl, moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide. See, e.g., U.S. Pat. Nos. 6,214,345 and 7,745,394, the contents of both of which are incorporated by reference in their entireties.

In one embodiment, the Linker Unit is as described in U.S. Pat. Nos. 6,214,345 and 7,745,394 and has formula:

wherein A is a Stretcher Unit,
a is 0 or 1,
each —W— is independently an Amino Acid Unit,
w is an integer ranging from 0 to 12,
Y is a Spacer Unit, and
y is 0, 1 or 2.

The Stretcher Unit (—A—), when present, is capable of linking an antibody to the Amino Acid Unit (—W—). The antibody has a functional group that can form a bond with a functional group of a Stretcher. Useful functional groups that can be present on an antibody, either naturally or via chemical manipulation include, but are not limited to, sulfhydryl (—SH), amino, hydroxyl, carboxy, the anomeric hydroxyl group of a carbohydrate, and carboxyl. In one aspect, the antibody functional groups are sulfhydryl and amino. Sulfhydryl groups can be generated by reduction of an intramolecular disulfide bond of an antibody. Alternatively, sulfhydryl groups can be generated by reaction of an amino group of a lysine moiety of an antibody using 2-iminothiolane (Traut's reagent) or another sulfhydryl generating reagent.

The Amino Acid Unit (—W—), when present, links the Stretcher Unit to the Spacer Unit if the Spacer Unit is present, links the Stretcher Unit to the compound of formula (I) if the Spacer Unit is absent, and links the antibody to the compound of formula (I) if the Stretcher Unit and Spacer Unit are absent.

$W_w$— is a dipeptide, tripeptide, tetrapeptide, pentapeptide, hexapeptide, heptapeptide, octapeptide, nonapeptide, decapeptide, undecapeptide or dodecapeptide unit. The Amino Acid may be any amino acid. In some embodiments, the Amino Acid Unit comprises natural amino acids. In other embodiments, the Amino Acid Unit comprises non-natural amino acids.

The Spacer Unit (—Y—), when present, links an Amino Acid Unit to the compound of formula (I) when an Amino Acid Unit is present. Alternately, the Spacer Unit links the Stretcher Unit to the compound of formula (I) when the Amino Acid Unit is absent. The Spacer Unit also links the compound of formula (I) to the antibody when both the Amino Acid Unit and Stretcher Unit are absent.

Suitable Spacer Units include, but are not limited to, a glycine-glycine unit; a glycine unit; p-aminobenzyl alcohol (PAB) unit or aromatic compounds that are electronically similar to the PAB group such as 2-aminoimidazol-5-methanol derivatives (Hay et al. (1999) Bioorg. Med. Chem. Lett. 9:2237) and ortho or para-aminobenzylacetals; spacers that undergo cyclization upon amide bond hydrolysis, such as substituted and unsubstituted 4-aminobutyric acid amides (Rodrigues et al., Chemistry Biology, 1995, 2, 223), appropriately substituted bicyclo[2.2.1] and bicyclo[2.2.2] ring systems (Storm, et al., J. Amer. Chem. Soc., 1972, 94, 5815) and 2-aminophenylpropionic acid amides (Amsberry, et al., J. Org. Chem., 1990, 55, 5867); and a branched bis(hydroxymethyl)styrene (BHMS) unit.

Examples of Linker Units, Stretching Units and Amino Acid Units are described in U.S. Pat. Nos. 6,214,345 and 7,745,394.

In some embodiments, $A_a$ is maleimidocaproyl (mc).
In some embodiments, $W_w$ is Valine-Citrulline (ValCit).
In some embodiments, $Y_y$ is p-aminobenzyloxycarbonyl (PABC).
In some embodiments, $A_a$ is maleimidocaproyl, $W_w$ is Valine-Citrulline and $Y_y$ is p-aminobenzyloxycarbonyl (mcValCitPABC).

In some embodiments, the Linker Unit is selected from maleimidocaproyl; mcValCitPABC-, MalPegXC2-, AmPegXC2-, mcValCitPABCAmPegXC2-, Ma1PegXC2ValCitPABC-, 2BrAcPegXC2, my-, mb- me-, MalC6-, PFPCOPe2XC2ValCitPABC-, PFPCOPegXC2AmPegYC2-, PFPCOPegXC2AlaAlaAsnPABC-, PFPCOPegXC2-, PFPCOPegXC2AmPegYC2PABC-, mcGly-, AzCOC2Ph4AmCOPeg2C2-, AzCOC2Ph4AmPegIC1-, and AcLysValCitPABC-, each of which is described in U.S. Pat. No. 9,249,186.

The term "MalPegXC2-" refers to

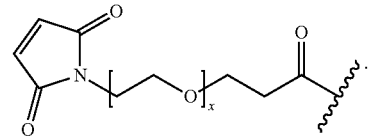

The term "AmPegXC2-" refers to

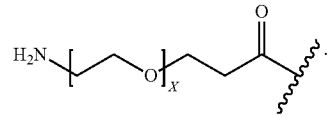

The term "mcValCitPABCAmPegXC2-" refers to
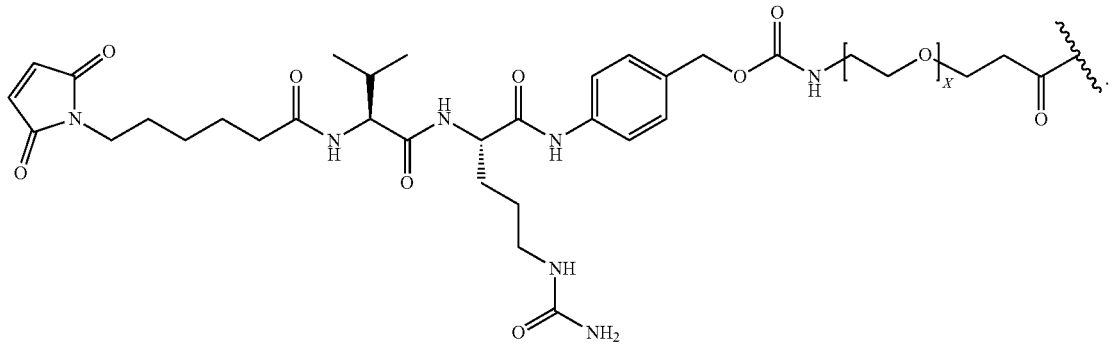
The term "Ma1PegXC2ValCitPABC-" refers to
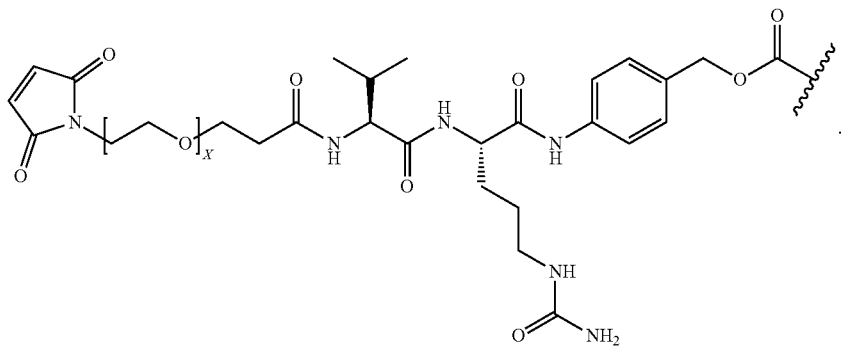
The term "2BrAcPegXC2" refers to
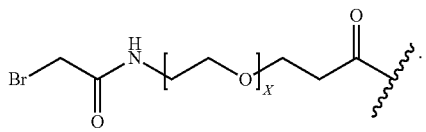
The term "mb" refers to
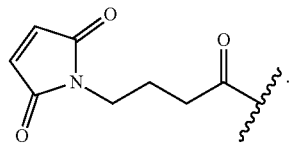
The term "mv-" refers to
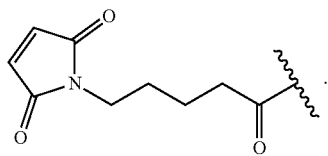 [SMILES: *C(=O)CCCCN1C(=O)C=CC1=O]
The term "me-" refers to
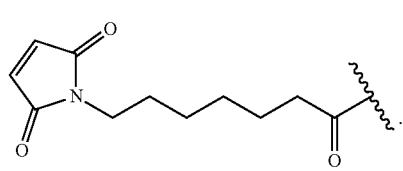 [SMILES: *C(=O)CCCCCCN1C(=O)C=CC1=O]

The term "MalC6-" refers to
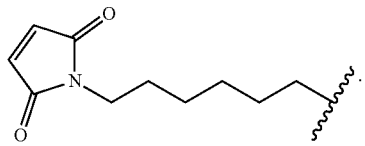 [SMILES: *CCCCCCN1C(=O)C=CC1=O]
The term "PFPCOPe2XC2ValCitPABC-" refers to
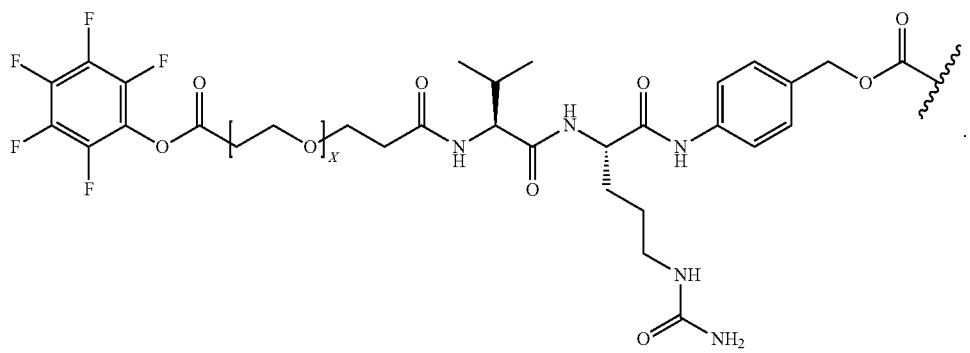
The term "PFPCOPegXC2AmPegYC2-" refers to
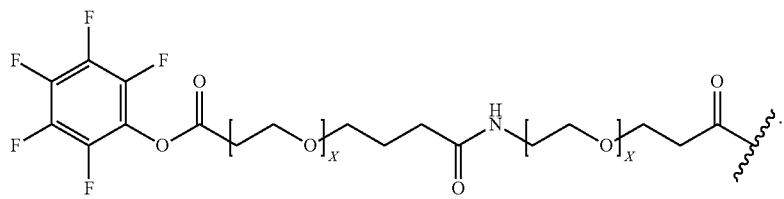
The term "PFPCOPegXC2AlaAlaAsnPABC-" refers to
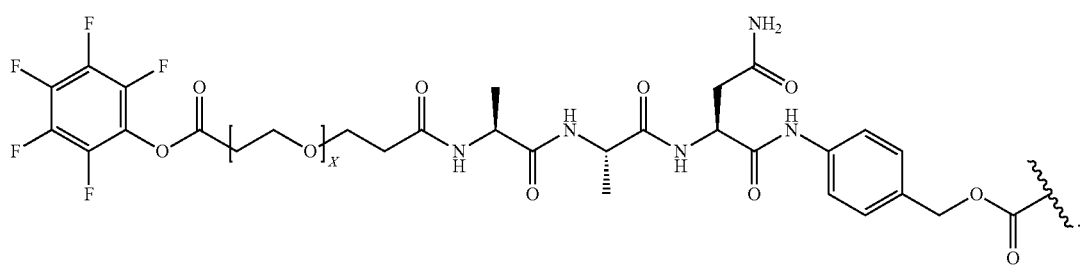

The term "PFPCOPegXC2-" refers to
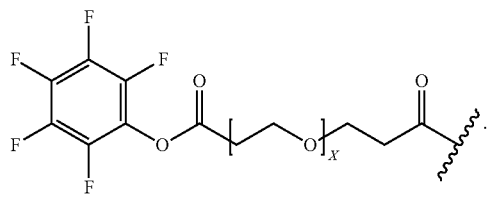
The term "PFPCOPegXC2AmPegYC2PABC-" refers to
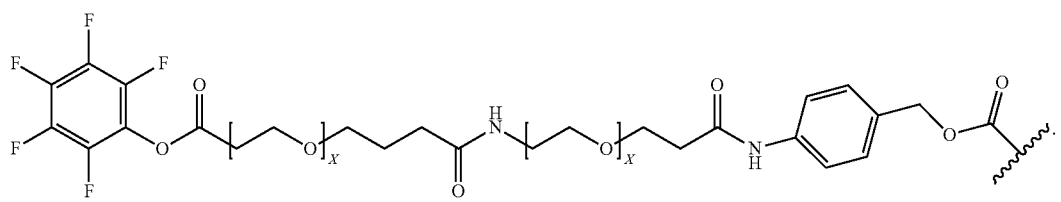
The term "mcGly-" refers to
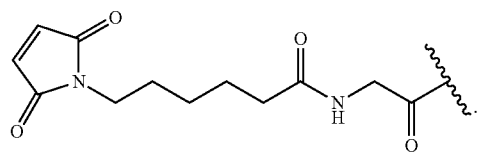 [SMILES: *C(=O)CNC(=O)CCCCCN1C(=O)C=CC1=O]
The term "AzCOC2Ph4AmCOPeg2C2-" refers to
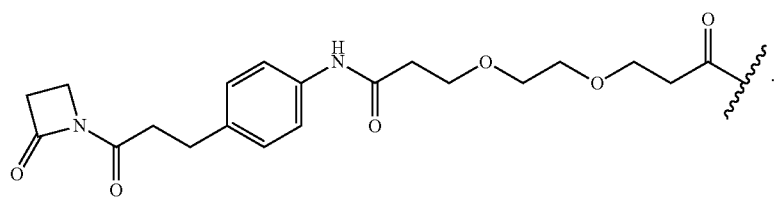 [SMILES: *C(=O)CCOCCOCCC(=O)Nc1ccc(CCC(=O)N2CCC2=O)cc1]
The term "AzCOC2Ph4AmPeglC1-" refers to
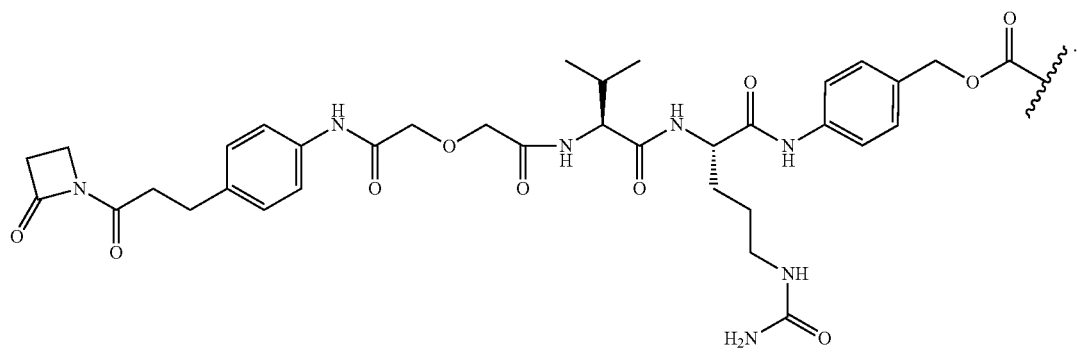 [SMILES: *C(=O)OCc1ccc(NC(=O)[C@H](CCCNC(N)=O)NC(=O)[C@@H](NC(=O)COCC(=O)Nc2ccc(CCC(=O)N3CCC3=O)cc2)C(C)C)cc1]

The term "AcLysValCitPABC-" refers to

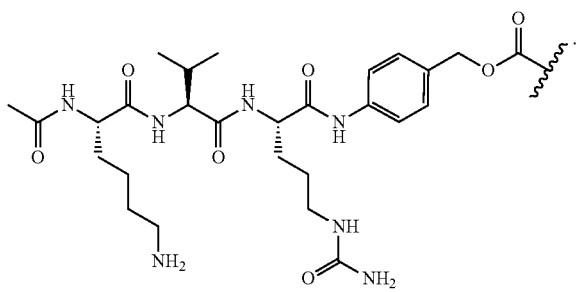 [SMILES: *C(=O)OCc1ccc(NC(=O)[C@H](CCCNC(N)=O)NC(=O)[C@@H](NC(=O)[C@H](CCCCN)NC(C)=O)C(C)C)cc1]

In a second embodiment, the present disclosure provides a compound of formula (Ia),

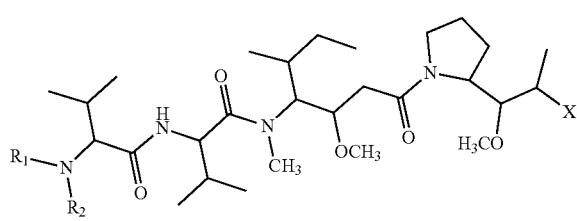

(Ia)

or a pharmaceutically acceptable salt thereof, wherein $R_1$, $R_2$, X are as described above in connection with the compound of formula (I); and
$R_4$ is

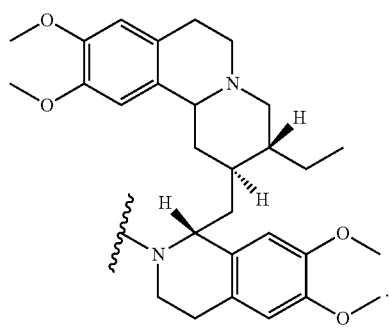

In one embodiment, the compound of formula (Ia) may be conjugated to an antibody, e.g., selected from the antibodies described above in connection with the compound of formula (I). The antibody may be conjugated to the compound of formula (Ia) in the manner described above in connection with the compound of formula (I).

In embodiments in which the compound of formula (Ia) is conjugated to an antibody through a Linker Unit, the Linker Unit may be selected from the Linker Units described above in connection with the compound of formula (I).

In a second embodiment, the present disclosure provides a compound of formula (Ib),

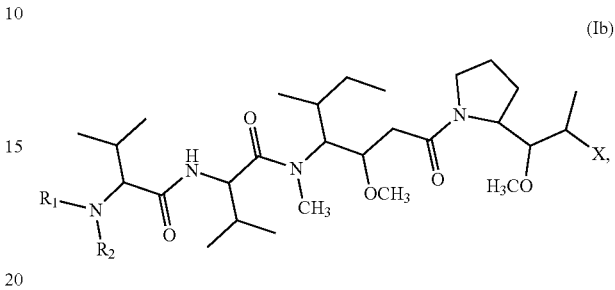

(Ib)

or a pharmaceutically acceptable salt thereof, wherein $R_1$ and $R_2$ are as described above in connection with the compound of formula (I);
X is —C(O)$R_4$, —C(O)NH—($C_{1-6}$ alkyl)-C(=O)—$R_4$, or —C(O)NH—($C_{1-6}$ alkyl)-$R_4$; and
$R_4$ is

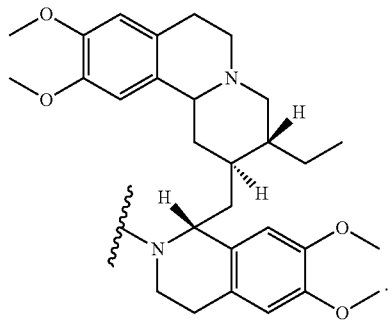

In one embodiment, the compound of formula (Ib) may be conjugated to an antibody, e.g., selected from the antibodies described above in connection with the compound of formula (I). The antibody may be conjugated to the compound of formula (Ib) in the manner described above in connection with the compound of formula (I).

In embodiments in which the compound of formula (Ib) is conjugated to an antibody through a Linker Unit, the Linker Unit may be selected from the Linker Units described above in connection with the compound of formula (I).

Representative compounds of formula (I) include:

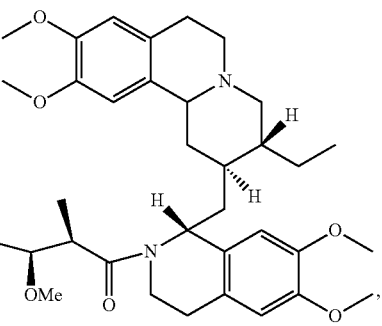

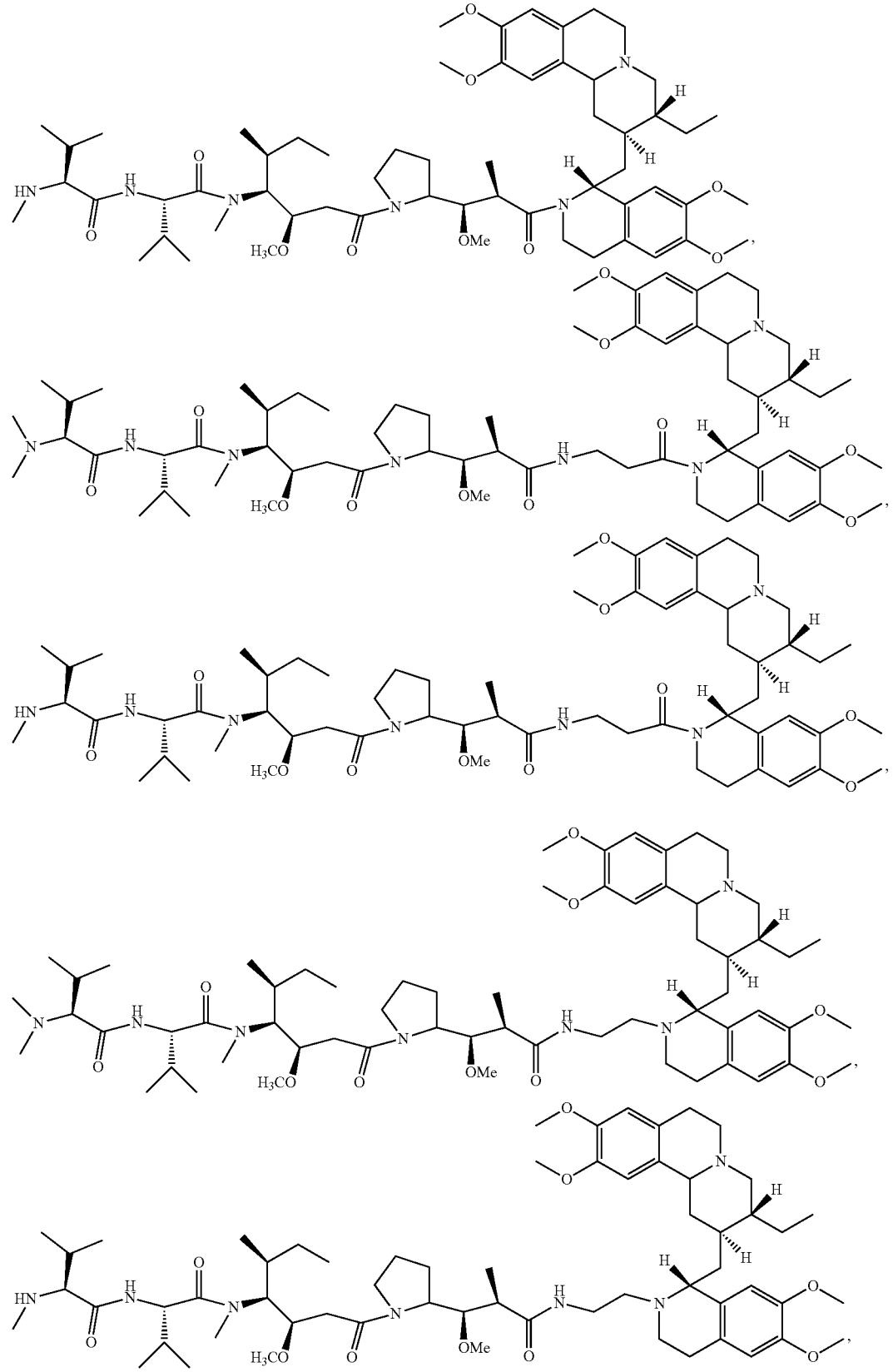
and pharmaceutically acceptable salts thereof.

In one embodiment, the compound is
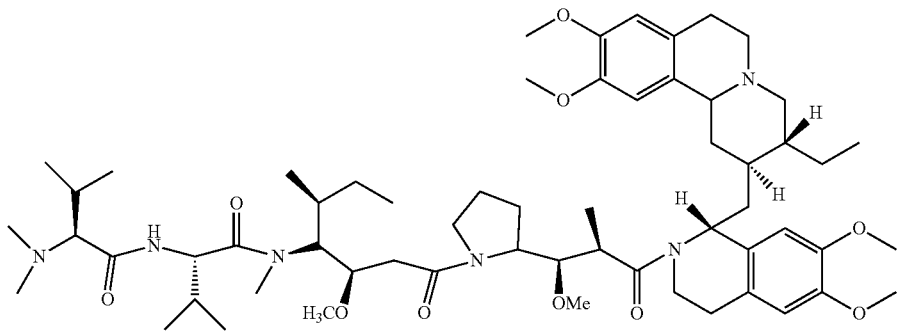
or a pharmaceutically acceptable salt thereof.
In one embodiment, the compound is
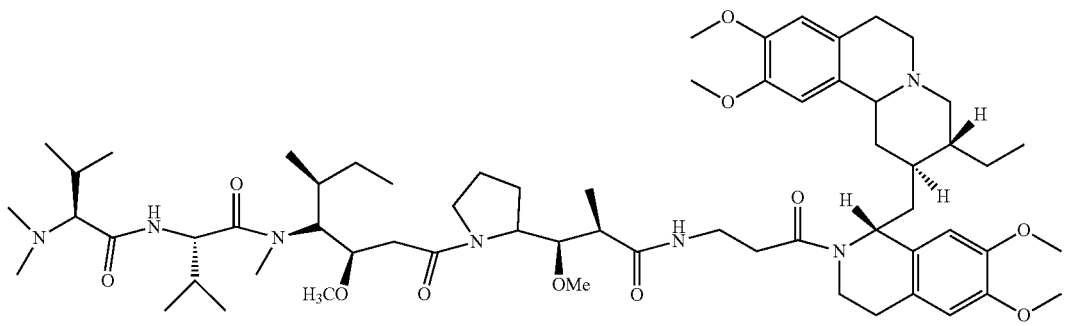
or a pharmaceutically acceptable salt thereof.
In another embodiment, the compound is
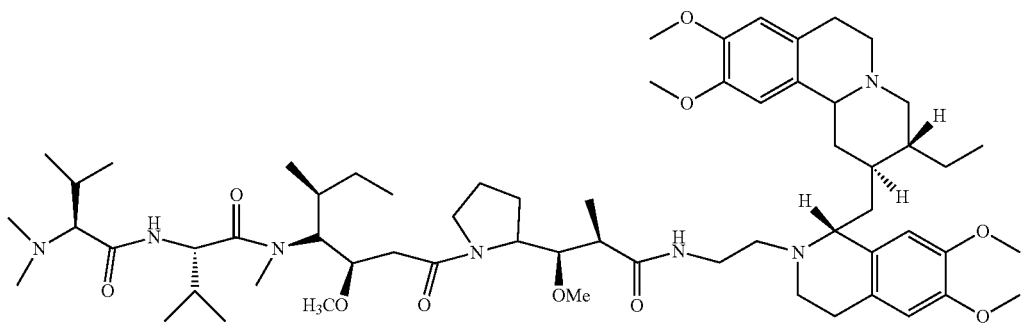
or a pharmaceutically acceptable salt thereof.

Additional representative compounds of formula (I) include:

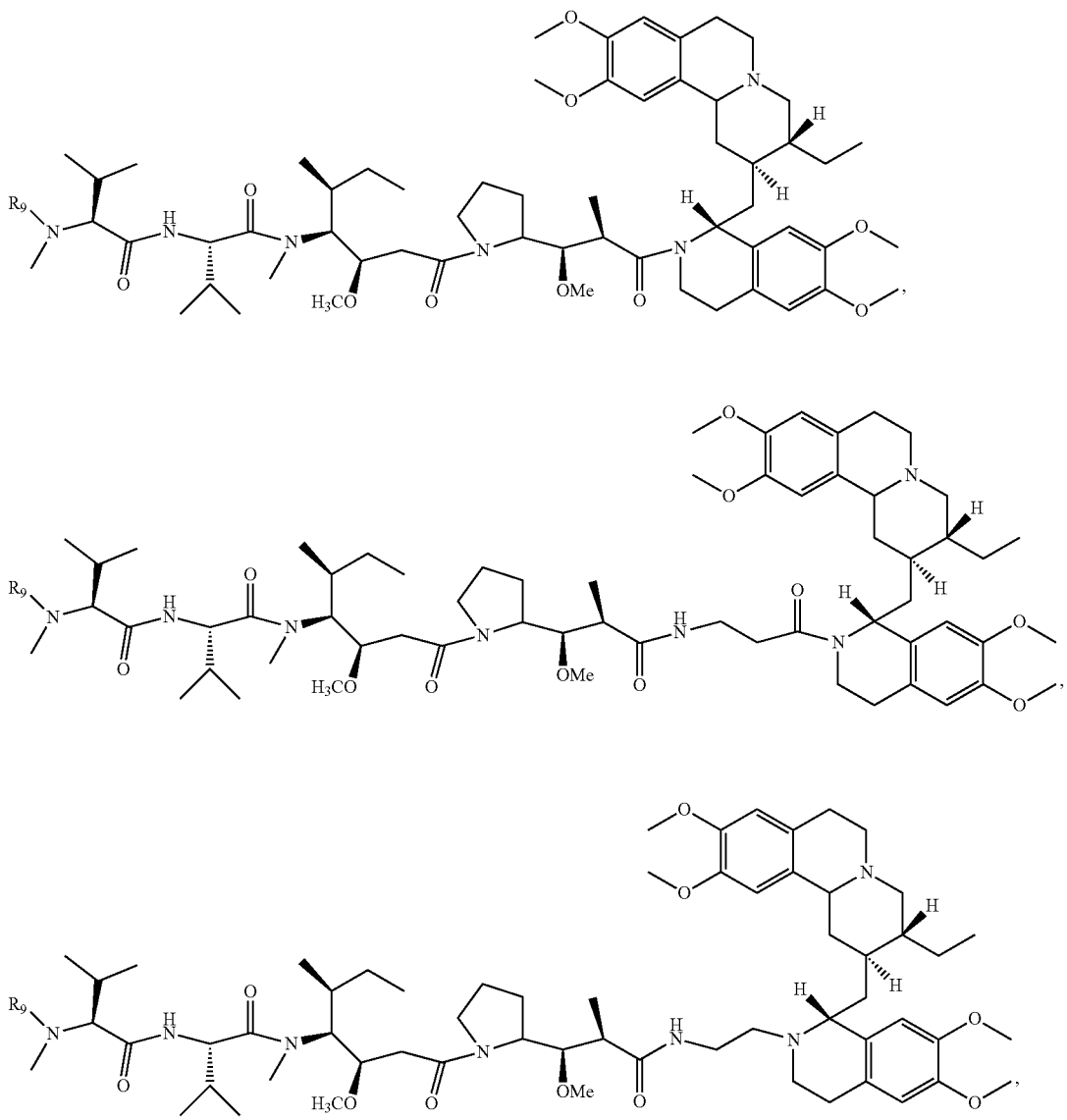

and pharmaceutically acceptable salts thereof, wherein
R₉ is a Linker Unit having formula:

$A_aW_wY_y$, $A_a$ is maleimidocaproyl, $W_w$ is Valine-Citrulline and $Y_y$ is p-aminobenzyloxycarbonyl.

Pharmaceutical Compositions

According to another embodiment, the present disclosure provides a pharmaceutical composition comprising a compound described herein or a pharmaceutically acceptable salt thereof and a pharmaceutically acceptable carrier.

The pharmaceutical composition of the disclosure may be formulated for administration in solid or liquid form, including those adapted for administration by oral, nasal, parenteral, rectal, topical, ocular, inhalation and intra-tumor administration. Parenteral administration includes subcutaneous injections, intravenous, intramuscular or intrasternal injection or infusion techniques. In one embodiment, the compositions are administered parenterally. In another embodiment, the compositions are administered intravenously.

The pharmaceutical composition of the disclosure may be in the form of a liquid, e.g., a solution, emulsion or suspension, pellets, powders, sustained-release formulations, or any other form suitable for use. The pharmaceutical composition may comprise sterile diluents such as water, saline solution, preferably physiological saline, Ringer's solution, isotonic sodium chloride, fixed oils such as synthetic mono- or diglycerides, which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates, phosphates or amino acids; agents for the adjustment of tonicity such as sodium chloride or dextrose; surfactants; preservatives; wetting agents; dispersing agents; suspending agents; stabilizers; solubilizing agents; local anesthetics, e.g., lignocaine; or isotonic agent.

It should be understood that a specific dosage and treatment regimen for any particular patient will depend upon a variety of factors, including the type of patient (e.g., human), the activity of the specific compound employed, the composition employed, the manner of administration, the age, body weight, general health, sex, diet, time of administration, rate of excretion, drug combination, and the judgment of the treating physician and the nature and the severity of the particular disorder being treated. The amount of active ingredients will also depend upon the particular compound in the composition. The amount of active ingredient can be determined by standard clinical techniques. In addition, in vitro or in vivo assays can optionally be employed to help identify optimal dosage ranges.

Preferably, the compositions are formulated so that a dosage of between about 0.01 to about 20 mg/kg body weight/day of the compound of formula (I) can be administered to a patient receiving the composition. In one embodiment, the dosage administered to the patient is between about 0.01 mg/kg and about 10 mg/kg of the patient's body weight. In another embodiment, the dosage administered to the patient is between about 0.1 mg/kg and about 10 mg/kg of the patient's body weight. In yet another embodiment, the dosage administered to the patient is between about 0.1 mg/kg and about 5 mg/kg of the patient's body weight. In yet another embodiment, the dosage administered is between about 0.1 mg/kg and about 3 mg/kg of the patient's body weight. In yet another embodiment, the dosage administered is between about 1 mg/kg and about 3 mg/kg of the patient's body weight.

The pharmaceutical compositions comprise an effective amount of a compound described herein such that a suitable dosage will be obtained. Typically, this amount is at least about 0.01% of a compound by weight of the composition. In a preferred embodiment, pharmaceutical compositions are prepared so that a parenteral dosage unit contains from about 0.01% to about 2% by weight of the compound of the disclosure.

For intravenous administration, the pharmaceutical composition may comprise from about 0.01 to about 100 mg of a compound described herein per kg of the patient's body weight. In one aspect, the composition may include from about 1 to about 100 mg of a compound described herein per kg of the patient's body weight. In another aspect, the amount administered will be in the range from about 0.1 to about 25 mg of a compound described herein per kg of body weight.

The pharmaceutical compositions of the disclosure may optionally further comprise a second therapeutic agent in a therapeutically effective amount. The second therapeutic agent includes those that are known and those discovered to be effective in treating cancer. In some embodiments, the second therapeutic agent may be selected from the group consisting of a tubulin-forming inhibitor, a topoisomerase inhibitor, and a DNA binder.

Methods of Use

According to another embodiment, the present disclosure provides methods of using the compounds described herein or pharmaceutical compositions thereof. The compounds and compositions are useful for killing or inhibiting the proliferation of tumor cells or cancer cells. The compounds and compositions are also useful for treating cancer in a patient.

In some embodiments, the present disclosure provides methods of killing or inhibiting the proliferation of tumor cells or cancer cells. In some embodiments, the method comprises contacting the tumor cells or cancer cells with a compound described herein, or a pharmaceutically acceptable salt thereof, in an amount effective to kill or inhibit the proliferation of the tumor cells or cancer cells. In alternate embodiments, the method comprises contacting the tumor cells or cancer cells with a pharmaceutical composition comprising a compound of formula (I) in an amount effective to kill or inhibit the proliferation of the tumor cells or cancer cells.

In some embodiments, the method further comprises contacting the cells with an effective amount of a second therapeutic agent or a pharmaceutical composition thereof. In one embodiment, the second therapeutic agent is selected from the group consisting of a tubulin-forming inhibitor, a topoisomerase inhibitor, and a DNA binder.

The cells may be contacted with the compound described herein and the second therapeutic agent simultaneously in either the same or different compositions or sequentially in any order. The amounts of compound described herein and the second therapeutic agent and the relative timings of their contact will be selected in order to achieve the desired combined effect.

In another embodiment, the present disclosure provides a method of determining inhibition of cellular proliferation by a compound described herein. The method comprises contacting cells in a cell culture medium with the compound described herein and measuring the cytotoxic activity of the compound, whereby proliferation of the cells is inhibited. In some embodiments, the method further comprises culturing the cells for a period from about 6 hours to about 5 days.

Suitable cell lines are known to those skilled in the art and include those used for evaluating other anticancer drugs. Such cell lines include, but are not limited to, BXPC-3 (pancreas); MCF-7 (breast); SF-268 (CNS); NCI-H460 (lung); KM20L2 (colon); DU-145 (prostate); 786-O, (renal cell carcinoma); Caki-1 (renal cell carcinoma); L428 (Hodgkin's disease); UMRC-3 (renal cell carcinoma); LP-1 (human myeloma); and U251 (glioblastoma). In some embodiments, the cells are obtained from a patient having a disease to be treated (e.g., cancer) or from a relevant cell line.

In another embodiment, the present disclosure provides a method of measuring cell viability in the presence of a compound described herein. The method comprises contacting cells in a cell culture medium with the compound of described herein, culturing the cells for a period from about 6 hours to about 5 days, preferably 96 hours; and measuring cell viability. In some embodiments, the cells are obtained from a patient having a disease to be treated (e.g., cancer) or from a relevant cell line.

In another embodiment, the present disclosure provides a method for treating cancer in a patient. In some embodiments, the method comprises administering to the patient a compound described herein, or a pharmaceutically acceptable salt thereof, in an amount effective to treat cancer. In other embodiments, the method comprises administering to the patient a composition comprising a compound described herein in an amount effective to treat cancer.

In some embodiments, the patient receives an additional treatment, such as radiation therapy, surgery, and chemotherapy with another chemotherapeutic agent or combinations thereof. In some embodiments, the compound of the disclosure is administered concurrently with the chemotherapeutic agent or with radiation therapy or with surgery. In other embodiments, the chemotherapeutic agent or radiation therapy or surgery is administered or performed prior or subsequent to administration of a compound of the disclosure.

In some embodiments, the method for treating cancer further comprises administering to the patient an effective amount of a second therapeutic agent, e.g., a chemotherapeutic agent. Any one or a combination of the chemotherapeutic agents, such a standard of care chemotherapeutic agent(s), can be administered. In some embodiments, the chemotherapeutic agent may be selected from the group consisting of a tubulin-forming inhibitor, a topoisomerase inhibitor, and a DNA binder.

The compound described herein, and the chemotherapeutic agent may be administered simultaneously in either the same or different pharmaceutical composition or sequentially in any order. The amounts of compound described herein, and the chemotherapeutic agent and the relative timings of their administration will be selected in order to achieve the desired combined effect.

In another embodiment, the present disclosure provides a method of inhibiting the growth of tumor cells that overexpress a tumor-associated antigen in a patient. In some embodiments, the method comprises administering to the patient a compound described herein conjugated to an antibody that is specific for said tumor-associated antigen, wherein the compound described herein is administered in amount effective to inhibit growth of tumor cells in the patient. In alternate embodiments, the method comprises administering to the patient a pharmaceutical composition comprising a compound described herein conjugated to an antibody that is specific for said tumor-associated antigen, wherein the compound described herein is administered in amount effective to inhibit growth of tumor cells in the patient. The method may optionally further comprises administering to the patient a chemotherapeutic agent, or a pharmaceutical composition thereof, in an amount effective to inhibit the growth of tumor cells in the patient.

In some embodiments, the compound sensitizes the tumor cells to the chemotherapeutic agent.

In some embodiments, the compound induces cell death. In other embodiments, the compound induces apoptosis.

In some embodiments, the tumor cells are associated with a cancer selected from the group consisting of breast, ovarian, stomach, endometrial, salivary gland, lung, kidney, colon, colorectal, thyroid, pancreatic, prostate, central nervous system and bladder cancer.

In some embodiments, the compound described herein is conjugated to an antibody selected from the group consisting of CD19, CD20, CD30, CD33, CD70, BCMA, Glypican-3, Liv-1 and Lewis Y.

Any compound or pharmaceutical composition described herein may be used in the methods of the present disclosure.

In some of the above methods, the compound described herein is administered to a patient in a composition comprising a pharmaceutically acceptable carrier. In some of these embodiments, the composition is administered intravenously. In certain embodiments, the compound is formulated in a unit dosage injectable form.

In preferred embodiments of each of the above methods, the patient is a human.

In an additional embodiment, the present disclosure provides the use of a compound of described herein in the manufacture of a medicament for the treatment of any of the above-mentioned cancers. It will be appreciated that a compound described herein, and one or more chemotherapeutic agents may be used in the manufacture of the medicament.

In additional embodiments, the present disclosure provides an article of manufacture comprising a compound described herein, a container, and a package insert or label indicating that the compound can be used to treat cancer characterized by the overexpression of at least one tumor-associated antigen.

The term "package insert" is used to refer to instructions customarily included in commercial packages of therapeutic products, that contain information about the indication(s), usage, dosage, administration, contraindications and/or warnings concerning the use of such therapeutic products.

In order that this invention be more fully understood, the following examples are set forth. These examples are for the purpose of illustration only and are not to be construed as limiting the scope of the invention in any way.

EXAMPLES

The compounds of this disclosure may be prepared by methods known to those skilled in the art, or the methods set forth below. By following the methods below, additional compounds of the disclosure can be prepared by modifying the choice of starting materials, reagents and reaction conditions as known to those skilled in the art.

General Experimental Procedures. Both N-Boc-dolaproine and Dov-Val-Dil.TFA were synthesized as described earlier.[10a-c] Emetine dihydrochloride was purchased from Aldrich and used as received. Other reagents including diethyl cyanophosphonate (DEPC) and anhydrous solvents were purchased from Acros Organics (Fisher Scientific) and Sigma-Aldrich Chemical Company and were used as received. Melting points are uncorrected and were determined with a Fisher Scientific melting point apparatus. The $^1$H and $^{13}$C NMR spectra were recorded on Varian Unity NOVA 400 and 500 and Bruker 400 NMR instruments in deuterated solvents. High-resolution mass spectra were obtained using an LCMS/MS_Agilent QTOF 6530 instrument at the ASU ilab core facility. For TLC, Analtech silica gel GHLF Uniplates were used and visualized with shortwave UV irradiation and an iodine chamber. For column chromatography, silica gel (230-400 mesh ASTM) from E. Merck (Darmstadt, Germany) and Sephadex LH-20 (GE Healthcare, Uppsala, Sweden) was employed.

Example 1

Synthesis of 2N'-(Dov-Val-Dil-Dap)-Emetine (Compound 5)

Scheme 1 depicts the synthesis of 2N'-(Dov-Val-Dil-Dap)-Emetine (Compound 5). The emetine dihydrochloride (1) was condensed with the N-protected amino acid Boc-Dap (2)[10a,b] in dimethylformamide using the coupling reagent 2-(1H-Benzotriazol-1-yl)-1,1,3,3-tetramethyluronium hexafluorophosphate (HBTU) to give following purification, the Boc-Dap-emetine amide. The Boc protecting group was removed using trifluoroacetic acid (TFA) to give the peptide-emetine TFA salt 3 in 40% yield. Coupling with Dov-Val-Dil.TFA fragment (4)[10c] using diethylcyanophosphonate (DEPC), followed by separation employing silica gel chromatography and subsequent purification with sephadex LH-20 using size exclusion chromatography, gave the peptide-emetine analogue Compound 5.

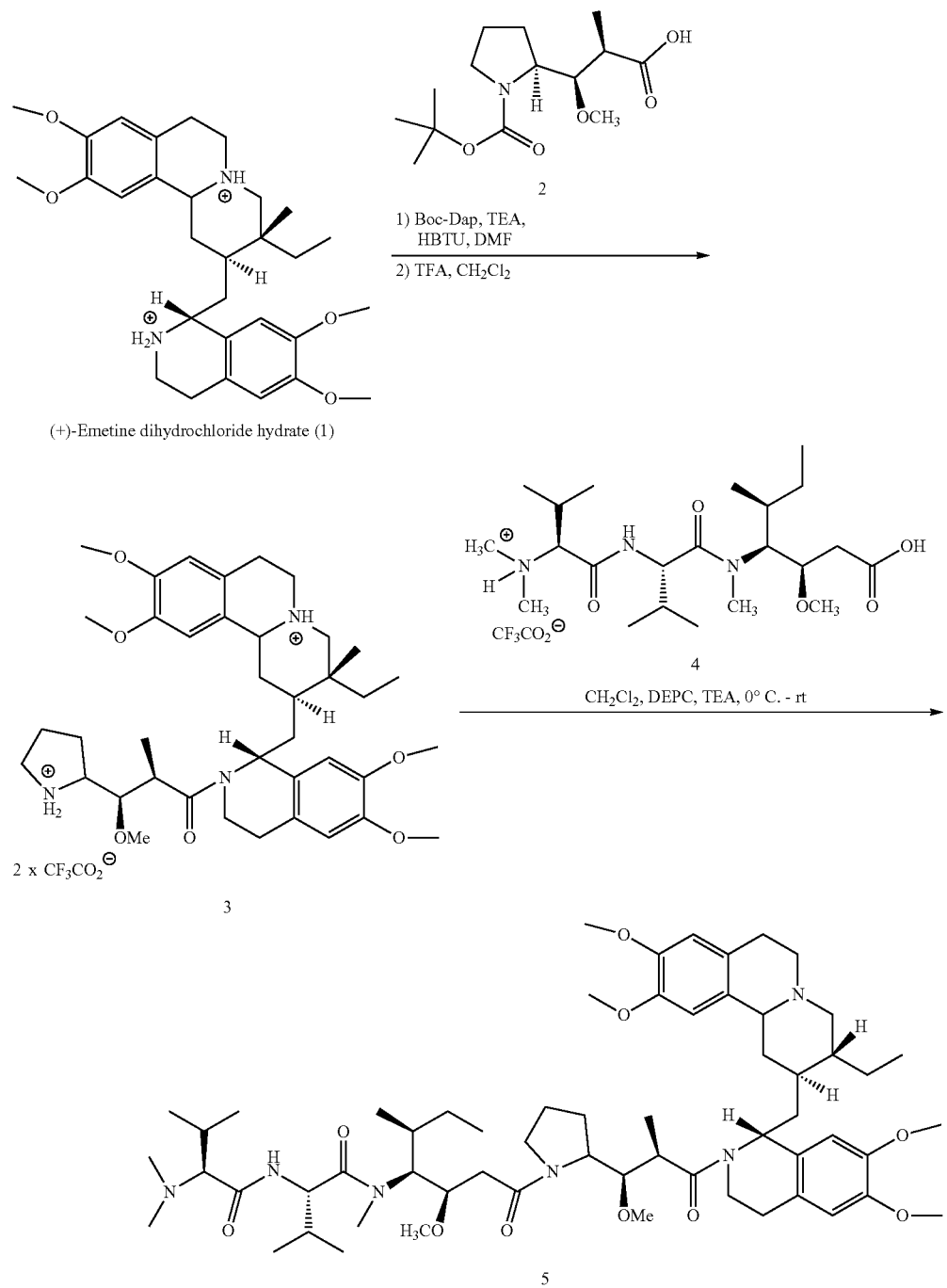

Scheme 1.

2'-N-(Dap)-emetine TFA salt (Compound 3): (−)-Emetine·2 HCl (1) (0.15 g, 0.27 mmol) was dissolved in dry DMF (3 mL) and TEA (75 µL, 0.54 mmol, 2 equiv) was added followed by a solution of Boc-Dap (2) (0.078 g, 0.27 mmol) in DMF (2 mL) and TEA (40 µL, 0.09 mmol). HBTU (0.21 g, 0.54 mmol, 2 equiv) was added and stirring was continued at 23° C. for 24 h. Ethyl acetate (50 mL) was added and the organic layer was extracted with water (4×25 mL), followed by brine (25 mL), dried ($MgSO_4$) and concentrated to a crude solid, which was separated using silica gel flash chromatography eluting with a gradient ($CH_2Cl_2$: $CH_3OH$ 97:3→95:5→90:10) to give 2'-N-(Boc-dap)-emetine as a light yellow colored oil (0.148 g, 73% yield): TLC $R_f$ 0.5 ($CH_2Cl_2$:$CH_3OH$ 92:8); (+)HRESIMS m/z 750.4716 $(M+H)^+$ (Calcd for $C_{43}H_{64}N_3O_8$, 750.4688).

Boc-dap-emetine (0.148 g, 0.197 mmol) was then dissolved in dry $CH_2Cl_2$ (2 mL) and TFA (0.5 mL, 0.74 g, 6.53 mmol, 33 equiv) was added. The reaction proceeded for 2 h under an atmosphere of $N_2$ before being concentrated to a brown oil. The oil was separated using size exclusion chromatography with sephadex LH20 eluting with methanol to give 3 as a yellow solid (83 mg, 40% from boc-dap): $^1$H NMR (CDCl$_3$, 400 MHz) δ 9.2 (1H, bs), 8.89 (1H, bs), 6.93 (1H, s), 6.55 (1H, s), 6.54 (1H, s), 6.52 (1H, s), 5.73 (1H, broad d, J=9.8 Hz), 3.97 (2H, m), 3.90 (3H, s), 3.87 (1H, m), 3.82 (3H, s), 3.79 (9H, s), 3.73-3.59 (3H, m), 3.50 (1H, m), 3.42 (1H, m), 3.33 (1H, m), 3.21 (1H, m), 3.18-3.08 (2H, m), 3.02 (1H, m), 2.89 (1H, m), 2.74 (2H, m), 2.20 (1H, t, J=12 Hz), 2.02 (1H, m), 1.89 (1H, m), 1.82-1.69 (3H, m), 1.66-1.48 (2H, m), 1.33-1.15 (5H, m), 0.83 (3H, t, J=7.3 Hz); $^{13}$C NMR (CDCl$_3$, 400 MHz) δ 173.1, 149.0, 148.7, 148.1, 148.0, 129.1, 124.2, 123.4, 123.2, 111.5, 111.4, 109.9, 108.4, 81.3, 64.4, 60.5 (2C), 59.4 56.5, 56.2, 56.0 (2C), 52.0, 48.7, 45.1, 38.9, 38.8, 38.7, 38.6, 38.4, 36.5, 33.9, 29.1, 25.9, 23.7, 22.7, 16.1, 9.9; (+)-HRESIMS m/z 651.4222 (M+H)$^+$ (Calcd for C$_{38}$H$_{57}$N$_3$O$_6$, 651.4242).

2'-N-(Dov-Val-Dil-Dap)-Emetine (Compound 5). To a solution of TFA salt (3) (0.110 g, 0.144 mmol) and Dov-Val-Dil-TFA salt$^{10c}$ (4) (0.080 g, 0.147 mmol) in anhydrous CH$_2$Cl$_2$ (2 mL) under N$_2$ at 0° C. was added TEA (85 μL, 0.063 g, 4.3 equiv) and DEPC (30 μL, 0.198 mmol, 1.37 equiv). The reaction mixture was stirred for 7 h with warming to rt, then concentrated under reduced pressure to remove the solvent and dried under a high vacuum overnight. Separation using column chromatography and a gradient elution (EtOAc 100%→EtOAc:CH$_3$COCH$_3$(1:1) →ETOAc: MeOH (98:2→90:10%) followed by CH$_2$Cl$_2$: MeOH 90:10 column wash gave the crude product with TEA contamination. The crude product was dissolved in CH$_2$Cl$_2$ and extracted with water. The organic fraction was separated, dried (MgSO$_4$) and concentrated under reduced pressure to give the product as an off white/yellowish amorphous powder (108 mg; 71% yield): TLC R$_f$ 0.36 (CH$_2$Cl$_2$:MeOH 91:9%); This material was further purified on a sephadex LH-20 column (eluent: CH$_3$OH) to give 5 as an amorphous yellow solid: TLC R$_f$ 0.47 (DCM: MeOH 8%); mp 110-112° C.; $^1$H NMR (CDCl$_3$, 400 MHz): Conformational isomers appear to be present in solution as the signal assigned to H-1' on emetine appears as two signals in a 1:0.3 ratio. δ 7.09 (1H, s), 7.00 (0.3H, m), 6.90 (1H, d, J=9 Hz), 6.82-6.75 (0.6 H, m), 6.63 (0.3 H, s), 6.61 (0.3 H, d, J=4.25), 4.78 (2H, m), 4.52 (0.3H, t, J=8.4 Hz), 4.21-4.11 (3H, m), 4.08 (3H, s, OCH$_3$), 3.98 (2H, m), 3.88-3.81 (11 H, m), 3.85, 3.84, 3.83 (3×Ar-OCH$_3$), 3.62 (1.6 H, m), 3.51-3.35 (8H, m), 3.40, 3.32 (2×OCH$_3$), 2.99 (3H, s, NCH$_3$), 2.93-2.82 (3H, m), 2.80 (1H, s), 2.78-2.69 (2H, m), 2.69-2.53 (3H, m), 2.52-2.15 (16 H, m), 2.13-1.86 (7H, m), 1.78-1.51 (6H, m), 1.42-1.66 (13 H, m), 1.12-0.64 (34 H, m). $^{13}$C NMR (CDCl$_3$, 400 MHz) δ 173.5, 173.2, 171.9, 169.6, 148.2, 147.9, 147.8, 131.5, 124.2, 111.5, 111.2, 110.3, 108.9, 86.8, 82.6, 77.4, 76.7, 62.0, 61.2, 60.6, 59.6, 59.2, 58.3, 56.9, 56.3, 56.1, 53.9, 53.6, 51.8, 48.5, 47.8, 43.1, 40.4, 39.7, 39.4, 38.7, 37.9, 35.9, 33.4, 32.1, 31.2, 31.1, 29.9, 29.5, 27.9, 25.9, 25.2, 23.7, 23.5, 20.3, 19.8, 18.3, 18.0, 16.4, 16.0, 15.7, 11.0; (+)HRESIMS m/z 1061.7300 (M+H)$^+$ (Calcd for C$_{60}$H$_{97}$N$_6$O$_{10}$, 1061.7261).

Example 2

Synthesis of Dov-Val-Dil-Dap-β-Ala-Emetine (Compound 9)

Scheme 1 depicts the synthesis of Dov-Val-Dil-Dap-β-Ala-Emetine (Compound 9). Following a synthetic procedure similar to that of Compound 5, Compound 9 was prepared via condensation of Boc-β-alanine with emetine using HBTU to give, following purification, β-ala-emetine (6). Removal of the Boc protecting group using TFA and subsequent purification the salt 7 was obtained. Condensation with Boc-Dap as described previously gave 8. The Dov-Val-Dil-Dap-β-Ala-Emetine (Compound 9) was then prepared as described for Compound 5.

Scheme 2

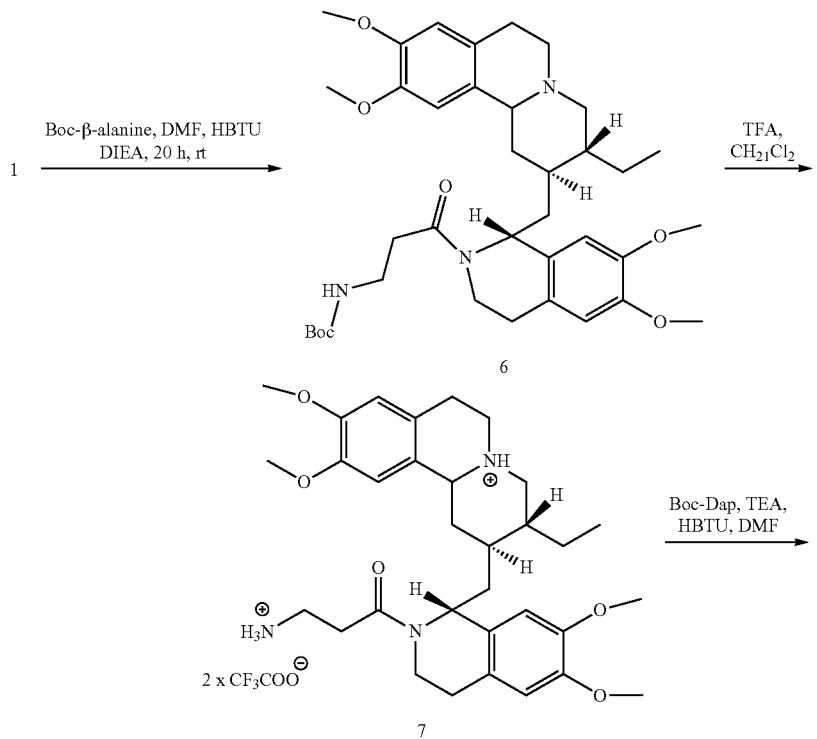

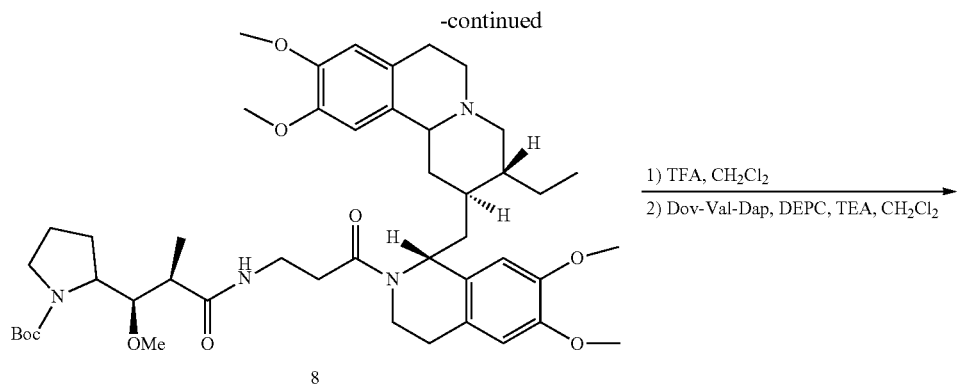

8

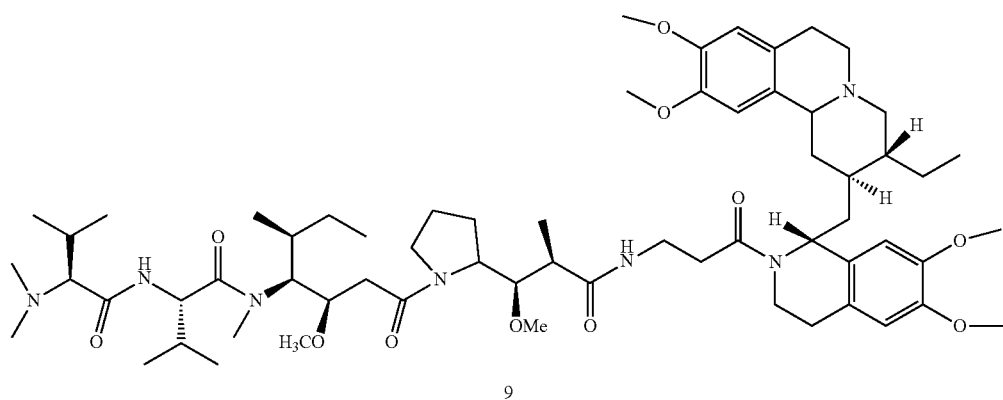

9

2'-(N-carboxy-β-alanyl)-tert-butyl emetine ester (Compound 6): N-Boc-β-alanine: A solution of β-alanine (0.2 g, 22.4 mmol) in 1M NaOH:THF (1:2) (30 mL) was cooled to 0° C. Ditertbutyldicarbonate (4.9 g, 22.4 mmol) was added and the reaction mixture stirred with warming to rt for 16 h. The solvent was removed under reduced pressure and the aqueous layer acidified to pH 2.0 with 4 M HCl and extracted with diethyl ether (5×10 mL). The combined organic layers were washed with brine and dried (Na$_2$SO$_4$), filtered and concentrated under reduced pressure to give N-Boc-□-alanine as a white crystalline solid which was collected using hexane and dried (2.0 g, 51% yield): mp 70° C. [Lit[3]. 71-72° C.]; $^1$H NMR (CDCl$_3$, 400 MHz) δ 11.19 (1H, bs, OH), 6.26, 5.13 (1H, bs, NH), 3.40 (2H, m), 2.58 (2H, m), 1.44 (9H, s). $^{13}$C-NMR (CDCl$_3$, 400 MHz) δ 177.6, 155.9, 79.8, 35.9, 34.5, 28.4. N-Boc-□-alanine (0.03 g, 0.158 mmol) was dissolved in anhydrous DMF (1 mL) at rt under N$_2$. HBTU (0.12 g, 0.316 mmol, 2 equiv) followed by DIEA (27 ml, 0.027 mL, 0.020 mg, 0.158 mmol) were added with stirring for 10 min. Emetine dihydrochloride (1) (0.09 g, 0.158 mmol) was then added to the reaction mixture. Stirring was continued for 20 h at rt and the reaction was monitored by TLC (CH$_2$Cl$_2$:CH$_3$OH 9:1). Ethyl acetate (10 mL) was added and the organic layer separated and washed with brine, dried (MgSO$_4$) and concentrated to a crude solid, 0.105 g. Separation by flash silica gel chromatography (eluent: CH$_2$Cl$_2$—CH$_3$OH (9:1) gave 6 as a yellow foam solid (59 mg, 57%) which was further purified on sephadex LH-20 (eluent: CH$_3$OH): TLC R$_f$ 0.53 (CH$_2$Cl$_2$:CH$_3$OH 9:1); $^1$H (CDCl$_3$, 400 MHz) δ 6.95 (1H, s), 6.54 (2H, m), 6.52 (1H, s), 5.81 (1H, dd, J=12.2, 3.3), 5.29 (1H, m, NH), 3.92 (3H, s, OCH$_3$), 3.87 (1H, m), 3.82 (3H, s, OCH$_3$), 3.81(6H, s, 2×OCH$_3$), 3.47-3.36 (3H, m), 3.17-3.00 (5H, m), 2.89-2.82 (1H, m), 2.75-2.60 (4H, m), 2.56-2.46 (2H, m), 2.24-2.06 (2H, m), 1.69-1.54 (1H, m), 1.45-1.26 (11H, m), 1.33 (s, 3×CH$_3$), 1.23-1.15 (2H, m), 1.14-1.02 (1 H, m), 0.84 (3H, t, J=7.3 Hz); $^{13}$C (CDCl$_3$, 400 MHz) δ 170.7, 156.3, 148.0, 147.99, 147.8, 147.7, 130.5, 129.6, 125.9, 124.8, 111.7, 111.5, 110.2, 108.8, 79.4, 63.4, 61.4, 56.3, 56.2, 56.15, 56.12, 52.4, 49.2, 41.4, 39.6, 38.8, 37.9, 37.0, 36.8, 33.5, 29.0, 28.8, 28.6 (×3C), 23.6, 11.1; (+)HRESIMS m/z 652.3972 (M+H)$^+$ (Calcd for C$_{37}$H$_{54}$N$_3$O$_7$, 652.3962).

2'-N-(β-alanine)-emetine TFA salt (Compound 7). A solution of amide 6 (0.030 g, 0.046 mmol) in dry CH$_2$Cl$_{12}$ (1 mL) was stirred and cooled to 0° C. under N$_2$. Trifluoroacetic acid (TFA) (0.20 mL) was added and the reaction mixture stirred for 2 h at rt, then the solvent was removed under reduced pressure, toluene was added as an azeotrope to further concentrate and remove any residual TFA. The residue was purified on sephadex LH-20 (eluent: CH₃OH) to give 7 as a light yellow colored solid (16 mg, 53% yield); $^1$H (CDCl₃, 400 MHz) δ 6.83 (1H, s), 6.57 (2H, s), 6.50 (1H,s), 5.68 (1H, d, J=12 Hz), 4.21 (1H, m), 3.85, 3.83, 3.81 (3 H each, OCH₃), 3.64 (1H,s), 3.58 (1H, m), 3.45-3.37 (2H, m), 3.24-2.99 (6H, m), 2.97-2.82 (3H, m), 2.78 (1H, s), 2.76-2.68 (2H, m), 2.22 (1H, tJ=11.6 Hz), 1.75-1.53 (3H, m), 1.52-1.39 (2H, M), 2'-N-(Dov-Val-Dil-Dap-β-Ala)-Emetine (Compound 9). To as solution of Boc-Dap[10a,b] (0.16 g, 0.54 mmol) in anhydrous DMF (4 mL) was added TEA (76 μL, 0.06 g, 0.54 mmol) followed by HBTU (0.41 g, 1.08 mmol). The reaction mixture was stirred for 5 min before adding a solution of 7 (0.3 g, 0.34 mmol) in DMF (1 mL). The solution was stirred under N₂ for 16 h. Ethyl acetate (50 mL) was added and the organic layer was extracted with brine (2×50 mL), dried (MgSO₄) and concentrated under reduced pressure to a crude product. Separation was carried out using flash column chromatography on silica gel with a gradient elution system (CH₂Cl₂:MeOH 97:3%→95:5%) to give 2'-N-(boc-dap-□-ala)-emetine (8) as a yellow foam solid (0.12 g, 48% yield): $R_f$ 0.47 (CH₂Cl₂-MeOH, 94:6); (+) HRESIMS m/z 843.4894 (M+Na)⁺ (Calcd for C₄₆H₆N₄O₉Na, 843.4879). Compound 8 was deprotected with TFA (0.2 ml, 2.53 mmol, 21 equiv) in CH₂Cl₂ (2.5 mL) for 2 h at rt and concentrated with toluene as an azeotrope under reduced pressure to give the TFA salt. The salt was dissolved in CH₂Cl₂ (5 mL) and the solution cooled to 0° C. (ice bath). Dov-Val-Dil-TFA salt[10c] was then added followed by DEPC (22 μL, 0.144 mmol, 1.2 equiv) and TEA (0.42 g, 58 mL, 3.5 equiv). The reaction mixture was stirred at 0° C. for 6 h and monitored by TLC (CH₂Cl₂:MeOH 90:10), then concentrated under reduced pressure and dried further under a high vacuum overnight. The crude product was separated by column chromatography using gradient elution (CH₂Cl₂ 100%→CH₂Cl₂:MeOH 90:10) to give the product still contaminated with TEA. The product mixture was then dissolved in CH₂Cl₂, extracted with water and dried (MgSO₄) and under a high vacuum to give Compound 9 as an off-white amorphous solid (27 mg, 20% yield): $R_f$ 0.14 (CH₂Cl₂:MeOH 93:7); $^1$H (CDCl₃, 400 MHz) conformers observed δ 6.94 (1H, s), 6.92 (1H, m, NH), 6.73 (1H, t, J=5.9 Hz, NH)), 6.57 (1H, s), 6.55 (1H, s), 6.53 (1H, s), 5.77 (1H, dd, J=11.8, 3.4 Hz), 4.75 (1H, dd, J=9.6, 6.6 Hz), 4.10 (2H, m), 3.94 (3H, OCH₃), 3.93 (1H, m), 3.86 (1H, m), 3.84 (3H, s, OCH₃), 3.82 (6H, s, OCH₃), 3.77-3.64 (2H, m), 3.49-3.35 (4H, m), 3.33 (3H, s, OCH₃), 3.29 (3H, s, OCH₃), 3.30 (1H, m), 3.01 (3H, s, NCH₃), 2.95-2.81 (2H, m), 2.79-2.50 (7H, m), 2.45 (2H, m), 2.38 (1H, m), 2.36-2.20 (8H, m), 2.25 (s, NCH₃×2), 2.12-1.89 (4H, m), 1.76 (1H,m), 1.60 (2H, m), 1.40-0.77 (CH, CH₂, CH₃ overlapping peaks). $^{13}$C NMR (CDCl₃, 400 MHz) conformers observed δ 174.4, 173.9, 173.6, 171.8, 170.8, 170.6, 170.4, 170.1, 148.13, 148.0, 147.99, 147.9, 147.8, 130.4, 130.2, 125.6, 124.9, 124.7, 111.7, 111.5, 110.2, 108.9, 86.1, 82.4, 78.5, 76.5, 63.2, 61.8, 60.7, 59.3, 58.4, 58.1, 56.3, 56.28, 56.1, 56.08, 54.0, 53.8, 53.3, 52.0, 50.7, 49.7, 49.3, 47.9, 46.7, 45.8, 45.1, 44.4, 43.0, 40.8, 39.5, 38.9, 37.8, 37.6, 36.4, 35.8, 34.8, 33.5, 33.3, 32.1, 31.2, 29.9, 29.5, 28.7, 28.6, 27.9, 26.3, 25.9, 25.1, 25.08, 23.7, 23.5, 22.9, 20.3, 19.98, 19.7, 18.3, 18.0, 16.7, 16.0, 15.7, 15.6, 14.4, 14.3, 11.0, 10.9, 10.6, 8.79. (+)HRESIMS m/z 1132.7663 (M+H)⁺ (Calcd for C₆₃H₁₀₂N₇O₁₁ 1132.7632).

Example 3

Synthesis of 2'-N-(ethylamine-N-Dap-Dil-Val-Dov)-Emetine (Compound 10)

Scheme 3 depicts the synthesis of 2'-N-(ethylamine-N-Dap-Dil-Val-Dov)-Emetine (Compound 10). Direct N-alkylation of the 2-N' secondary amine derivative of emetine (Compound 1) was carried out using 4 equivalents of cesium carbonate as the base and 1.5 equivalents of Boc-protected amino ethyl bromide.[11] Following purification using silica gel chromatography and deprotection using TFA as previously described HRMS analysis of the reaction products suggested over-alkylation had occurred. A mixture of the N-alkylated emetine TFA salt along with an unknown side product was condensed with Boc-Dap using DEPC, deprotected and the resulting amino acid-ethylamine TFA salt mixture coupled with the Dov-Val-Dil TFA salt fragment as described previously. After purification on silica gel and size exclusion chromatography the peptide-emetine analogue (Compound 10) was obtained. No other reaction products were identified from the product mixture.

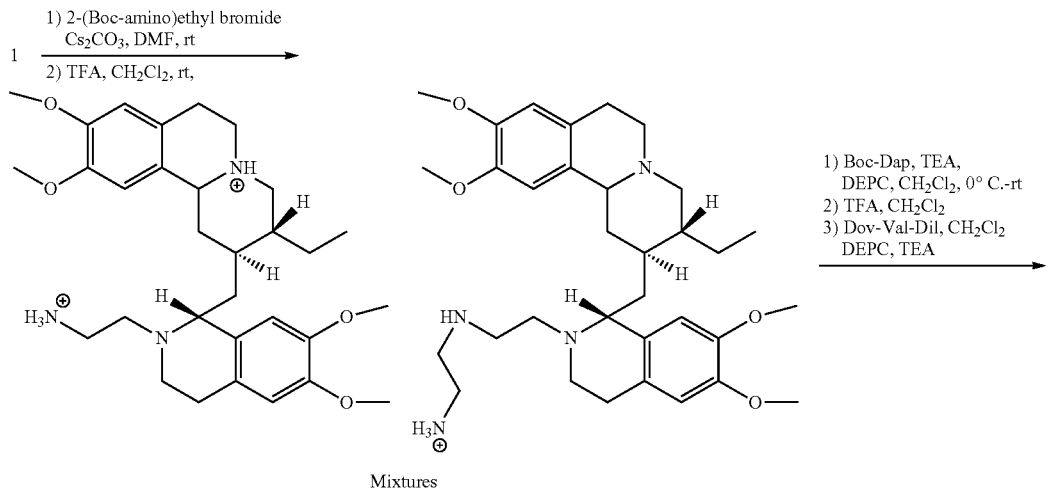

Mixtures

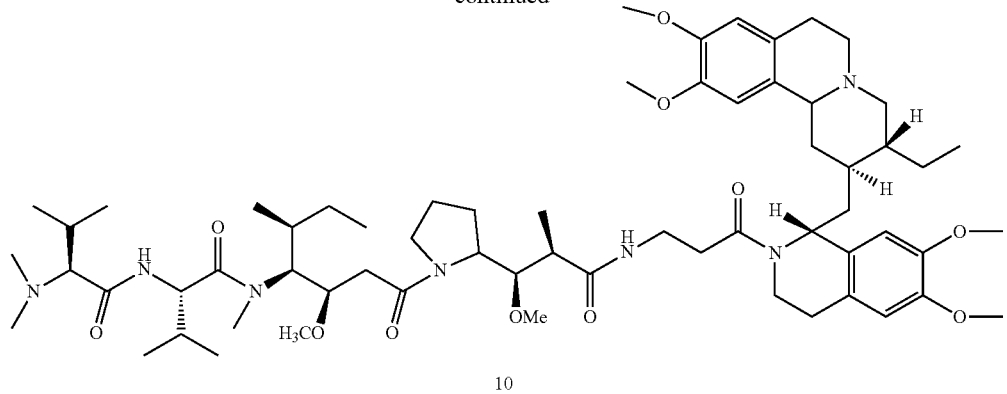

10

2'-N-(ethylamine-N-Dap-Dil-Val-Dov)-Emetine (Compound 10). 2'-(N-carboxy-ethylamine)-,tert-butyl Emetine ester mixtures: Emetine (0.075 g, 0.135 mmol) was dissolved in dry DMF (1 mL) and $Cs_2CO_3$ (0.092 g, 4 equiv) was added followed by 2-Boc-aminoethylbromide (0.045 g, 1.5 equiv). The mixture was stirred at rt under $N_2$ for 24 h. The reaction mixture was quenched with the addition of ethyl acetate (50 mL) and extracted with water (5×25 mL), dried ($MgSO_4$) and concentrated under reduced pressure. The resulting residue was separated by flash column chromatography (eluent: $CH_2Cl_2$:$CH_3OH$ 93:7) to provide a mixture of products (0.15 g) which were taken directly to deprotection using TFA without further purification. To a solution of the mixtures (0.15 g) in $CH_2Cl_2$ was added TFA (0.5 mL, 0.74 g, 6.53 mmol, 27 equiv) and the reaction mixture was stirred at rt for 2 h under $N_2$ before being concentrated under reduced pressure to a brown oil. The residue was purified by size exclusion chromatography on sephadex ($CH_3OH$ 100%) to give a brown solid (0.15 g). TLC $R_f$ 0.0 ($CH_2Cl_2$:MeOH:$NH_4OH$, 94:4:1). NMR data was not useful as peaks were broadened. (+)HRESIMS m/z 263.1782 $(M+2H)^{2+}$ (calcd for $C_{31}N_{48}N_3O_4$263.1817); 525.3522 $(M+H)^+$; (calcd for $C_{31}H_{47}N_3O_4$; 525.3561) and 567.3925 $(M+H)^+$ (calcd for $C_{33}H_{51}N_4O_4$ 567.3905)$^+$ The TFA salt mixture was carried forward without further attempts at separation. 2'-N(ethylamine-N-Dap-Dil-Val-Dov)-Emetine (Compound 10). To a solution of the ethylamine-emetine TFA salt mixtures (0.15 g) in dry $CH_2Cl_2$ (2 mL) was added TEA (0.15 ηL, 1.08 mmol, 6 equiv) and the solution cooled to 0° C. Boc-Dap (0.078 g, 0.27 mmol, 1.53 equiv) and DEPC (0.05 mL, 0.54 g, 0.33 mmol, 1.9 equiv) were added and stirring was continued for 6 h, then the reaction was concentrated under reduced pressure and separated using silica gel chromatography with gradient elution ($CH_2Cl_2$:$CH_3OH$ 95:5→90:10) followed by purification on sephadex LH20 (eluent: $CH_3OH$) to give a brown solid (77 mg). The solid was dissolved in anhydrous $CH_2Cl_2$ (1 mL) and TFA (0.5 mL) was added with stirring for 1.5 h, then concentrated under reduced pressure to give a TFA salt mixture which was stirred together with Dov-Val-Dil-TFA (0.077 g, 0.142 mmol, 2.2 equiv) in anhydrous $CH_2Cl_2$ under $N_2$ at 0° C. TEA (0.085 mL, 0.063 g, 0.61 mmol, 10 equiv) and DEPC (0.03 mL, 0.032 g, 0.198 mmol, 3 equiv) were added, and the reaction mixture stirred for 6 h at 0° C., then concentrated and extracted with $CH_2Cl_2$. The organic layer was washed with water and dried ($MgSO_4$). The water fraction was made basic to pH 10 with the addition of 2N NaOH and back extracted with $CH_2Cl_2$. The organic extract was then concentrated, dried and separated by chromatography on silica gel using a gradient elution ($CH_2Cl_2$ 100%→$CH_2Cl_2$:$CH_3OH$ 96:4) to give the product 10 as a brown solid (17.7 mg). $^1$H NMR ($CDCl_3$, 400 MHz) δ 6.92 (1H, m), 6.75 (1H, m), 6.65 (1H, s), 6.56 (1H, s), 6.53 (1H, s), 6.43 (1H, s), 4.76 (2H, m), 4.11 (2H, m), 3.92 (1H, m), 3.82 (6H s), 3.80 (3H, s), 3.79 (3H, s), 3.69 (1H, m), 3.58 (1H, m), 3.49-3.21 (11 H, m), 3.18-3.04 (4 H, m), 3.00 (3H, s), 2.92-2.80 (2H, m), 2.76-2.60 (3H, m), 2.59-2.33 (6H, s), 2.24 (6H, s), 2.20-2.11 (2H, m), 2.09-1.90 (4H, m), 1.81-1.77 (2H, m), 1.70-1.57 (2H, m), 1.40-1.20 (4H, m), 1.20-1.07 (5H, m), 1.02-0.85 (20 H, m), 0.80 (3H, t, J=7.2 Hz). $^{13}$C NMR ($CDCl_3$, 120 MHz) multiple signals represent conformational isomers, δ 173.6, 173.5, 173.4, 173.3, 173.2, 171.7, 171.6, 170.4, 170.1, 147.7, 147.7, 147.6, 147.5, 147.4, 130.2, 130.14, 130.12, 130.1, 129.1, 126.3, 126.2, 125.9, 125.3, 125.0, 111.7, 111.5, 110.7, 108.2, 86.4, 82.2, 77.2, 76.4, 61.6, 61.1, 61.0, 60.4, 59.0, 58.7, 58.3, 58.2, 58.0, 57.0, 56.6, 56.2, 56.0, 55.9, 53.8, 51.8, 47.7, 43.8, 42.8, 40.6, 40.2, 37.7, 37.2, 33.2, 31.0, 25.7, 25.0, 24.9, 23.6, 23.5, 22.0, 20.1, 19.8, 19.6, 18.2, 17.9, 17.8, 16.6, 16.5, 15.9, 15.5, 15.3, 14.4, 14.0, 10.9, 10.8. (+)HRESIMS m/z $(M+H)^+$1104.7726 (Calcd for $C_{62}H_{102}N_7O_{10}$, 1104.7683).

Example 4

Inhibition of Human Cancer Cell Growth

Cancer Cell Line Procedures. Human cancer cell growth inhibition was measured using the standard sulforhodamine B assay of the U.S. National Cancer Institute, as previously described.[12] Briefly, cells in a 5% fetal bovine serum/RPMI1640 medium were inoculated in 96-well plates and incubated for 24 h. That was followed by serial dilutions of the compounds added. Forty-eight hours later the plates were fixed with trichloroacetic acid, stained with sulforhodamine B, and read with an automated microplate reader.

Next, growth inhibition of 50% ($GI_{50}$ or the drug concentration causing a 50% reduction in the net protein increase) was calculated from optical density data with Immunosoft® software.

TABLE 1

Human Cancer Cell Lines (GI50 µg/mL [nM]), Growth Inhibition of emetine dihydrochloride (1), Dap-emetine TFA (3), 2N'-(Dov-Val-Dil-Dap)-Emetine (5), intermediates 6-8, 2N'-(Dov-Val-Dil-Dap-β-Ala-)-Emetine (9) and 2N'-(Dov-Val-Dil-Dap-Ethylamino)-Emetine (10).

| Compound | BXPC-3 | MCF-7 | SF-268 | NCI-H460 | KM20L2 | DU-145 |
|---|---|---|---|---|---|---|
| 1 | 0.031 | 0.030 | 0.022 | 0.022 | 0.026 | 0.02 |
|   | [56.0] | [54.2] | [39.7] | [39.7] | [47.0] | [36.1] |
| 3 | 2.1 | 1.4 | 3.2 | 5.0 | 3.0 | 3.0 |
|   | [2393] | [1596] | [3647] | [5699] | [3419] | [3419] |
| 5 | 0.41 | 0.038 | 0.032 | 0.21 | 0.038 | 0.013 |
|   | [386.5] | [35.82] | [30.17] | [198.0] | [35.82] | [12.26] |
| 6 | >10 | 10 | >10 | >10 | >10 | >10 |
| 7 | 10.3 | >10 | >10 | >10 | >10 | 10.1 |
| 8 | >10 | >10 | >10 | >10 | >10 | 10.0 |
| 9 | 4.3 | 0.18 | 0.21 | 3.2 | 0.22 | 0.11 |
|   | [3799] | [159.0] | [185.6] | [2827] | [194.4] | [97.19] |
| 10 | 2.1 | 0.13 | 0.30 | 5.0 | 0.40 | 0.20 |
|   | [1902] | [117.8] | [271.8] | [4530] | [362.4] | [181.2] |

[a] Cancer cell lines in order: pancreas (BXPC-3); breast (MCF-7); CNS (SF-268); lung (NCI-H460); colon (KM20L2); prostate (DU-145).

Table 1 summarizes a series of cancer cell line growth inhibition experiments. It was found that in all six cell lines the TFA-Dap-emetine salt (Compound 3) showed a 100-fold decrease in activity compared to emetine. However, 2N'-(Dov-Val-Dil-Dap)-Emetine (Compound 5) showed cytotoxicity comparable to that of emetine in four of the six cell lines with the BXPC-3 cell line showing a 10-fold decrease. This suggests that either there was no steric hindrance impeding ubiquitous aminopeptidases from cleaving the peptide-emetine substrate between Dap and emetine to release free emetine during cellular uptake, or the 2N'-(Dov-Val-Dil-Dap)-emetine had biological activity comparable to emetine despite the N-2' position being blocked.

Compounds 6, 7 and 8 were inactive suggesting no release of emetine by peptidases. Biological activity reemerged when the Dov-Val-Dil-Dap peptide sequence was completed with Compounds 9 and 10. There was only a 10-fold decrease in biological activity in four cell lines when β-alanine and ethylamine were introduced between the Dap amino acid and emetine respectively when compared to both emetine and Compound 5.

REFERENCES

The following references are hereby incorporated by reference in their entireties:

(1) (a) For Antineoplastic agents 606 see: Pettit, G. R.; Melody, N.; Chapuis, J.-C. *J. Nat. Prod.* 2018, 81, 458-464. (b) Junior W. S. F.; Cruz, M. P.; dos Santos, L. L.; Mederios, M. F. T. *J. Herb. Med.* 2012, 2, 103-112 (c) Wiegrebe, W.; Kramer, W. J.; Shamma, M. *J. Nat. Prod,* 1984, 47, 397-408

(2) Vedder, E. B. *J. Trop. Med. and Hyg.* 1912, 15, 313.

(3) (a) Akinboye, E. S.; Bakare, O. *The Open Nat. Prod. J.* 2011, 4, 8-15. (b) Grollman, A. P. *Proc. Natl. Acad. Sci. USA,* 1966, 56, 1867-1874. (c) Busonero, C.; Leone, S.; Acconcia, F.; *Cell. Oncol.* 2017, 40, 299-301.

(4) (a) Miller, S. C.; Huang, R.; Sakamuru, S.; Shukla, S. J.; Attene-Ramos, M. S.; Shinn, P.; Van Leer, D.; Leister, W.; Austin. C. P.; Xia, M. *Biochem. Pharmacol.* 2010, 79, 1272-1280. (b) Boon-Unge, K.; Yu, Q.; Zou, T.; Zhou, A.; Govitrapong, P.; Zhou, J. *J. Chem. Biol.* 2007, 14, 1386-1392.

(5) (a) Jindorf, W. R.; Johnson, R. K.; Donahue, J. D. *Arch. Biochem. Biophys.* 1969, 134, 233-241. (b) Zhou, Y. D.; Kim, Y. P.; Mohammed, K. A.; Jones, D. K.; Muhammad, I.; Dunbar, D. C.; Nagle, D. G. *J. Nat. Prod.,* 2005, 68, 947-950.

(6) (a) Akinboye, E. S.; Rosen, D. M.; Denmeade, S. R.; Kwabi-Addo, B.; Bakare, O. *J Med Chem.* 2012, 55, 7450-7459. (b) Akinboye, E. S.; Bamji, Z. D; Kwabi-Addo, B.; Ejeh, D.; Copeland, R. L.; Denmeade, S. R.; Bakare, O. *Bioorg Med Chem.* 2015, 23, 5839-5845. (c) Bamji, Z. D.; Washington, K. N.; Akinboye, E. S.; Bakare, O., Kanaan, Y. M.; Copeland, R. L. *Anticancer Res.* 2015, 35, 4723-4732. (d) Akinboye, E. S.; Brennen, W. N.; Rosen, D. M.; Bakare, O.; Denmeade, S. R. *Prostate.* 2016, 76, 703-714. (e) Akinboye, E. S.; Rosen, M. D.; Bakare, O.; Denmeade, S. R. *Bioorg & Med Chem.,* 2017, 25, 6707-6717.

(7) (a) Pettit, G. R.; Gupta, S. K. *Can. J. Chem,* 1967, 45, 1600-1604. (b) Pettit, G. R.; Gupta, S. K. *Can. J. Chem,* 1967, 45, 1561-1566.

(8) (a) Pettit G. R.; Srirangam, J. K.; Barkoczy, J.; Williams, M. D.; Boyd, M. R.; Hamel, E.; Pettit, R. K.; Hogan, F.; Bai, R.; Chapuis, J-C.; McAllister, S.; Schmidt, J. M. *Anti-Cancer Drug Design,* 1998, 13, 243-277. (b) Pettit G. R.; Kamano, Y.; Hearld, C. L.; Tuinman, A. A.; Boettner, F. E.; Kizu, H.; Schmidt, J. M.; Baczynsyi, L.; Tomer, K. B.; Botems, R. J. *J. Am. Chem. Soc.* 1987, 109, 6883-6885.

(9) (a) Pettit, G. R.; Melody, N.; Chapuis, J.-C. *J. Nat. Prod.* 2018, 81, 451-457 (b) Pettit, G. R.; Melody, N.; Chapuis, J.-C. *J. Nat. Prod,* 2017, 80, 2447-2452 (c) Pettit, G. R.; Melody, N.; Chapuis, J.-C. *J. Nat. Prod,* 2017, 80, 692-698 (d) Pettit, G. R.; Hogan, F.; Toms, S. *J. Nat. Prod.* 2011, 74, 962-968.

(10) (a) Pettit, G. R.; Singh, S. B.; Herald, D. L.; Lloyd-Williams, P.; Kantoci, D.; Burkett, D. D.; Barkoczy, J.; Hogan, F.; Wardlaw, T. R. *J. Org. Chem.* 1994, 59, 6287-6295. (b) Pettit, G. R.; Grealish, M. P. *J. Org. Chem.* 2001, 66, 8640-8642. (c) Pettit, G. R.; Srirangam, J. K.; Singh, S. B.; Williams, M. D.; Herald, D. L.; Barkoczy, J.; Kantoci, D.; Hogan, F. *J. Chem. Soc., Perkin Trans.* 1 1996, 859-863.

(11) Castillo, J-C.; Orrego-Hernandez, J.; Portilla, J.; *Eur. J. Org. Chem.* 2016, 3824-3835.

(12) Monks, A.; Scudiero, D.; Skehan, P.; Shoemaker, R.; Paull, K.; Vistica, D.; Hose, C.; Langley, J.; Cronise, P.; Viagro-Wolff, A.; Gray-Goodrich, M.; Campbell, H.; Mayo, J.; Boyd, M. J. Natl. Cancer Inst. 1991, 83, 757-766.

(13) International PCT publication WO 2019/094709.

(14) International PCT publication WO 2017/019489.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present invention is not limited to the specific embodiments illustrated herein but is limited only by the following claims.

What is claimed is:

1. A compound of formula (I):

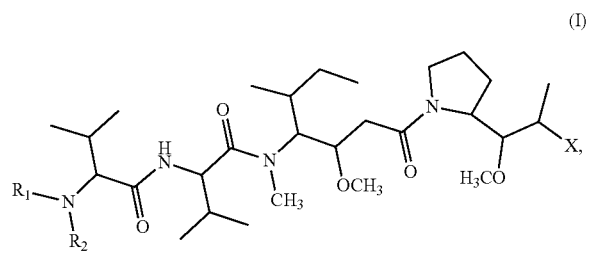

or a pharmaceutically acceptable salt thereof, wherein
$R_1$ is selected from H, $(C_1-C_6)$ alkyl, $(C_2-C_6)$ alkenyl, $(C_2-C_6)$ alkynyl, a Protecting Group or a Linker Unit;
$R_2$ is selected from H, $(C_1-C_6)$ alkyl, $(C_2-C_6)$ alkenyl or $(C_2-C_6)$ alkynyl;
X is —C(O)$R_4$, —C(O)NH—$(C_{1-6}$ alkyl)-C(=O)—$R_4$, —C(O)NH—$(C_{1-6}$ alkyl)-$R_4$, —$(C_{1-6}$ alkyl)-C(=O)—$R_4$, —$(C_{1-6}$ alkyl)-$R_4$, —$(C_{1-6}$ alkyl)S(O)—$R_4$, —$(C_{1-6}$ alkyl)-OS(O)—$R_4$, —$(C_{1-6}$ alkyl)-OS(O)O—$R_4$, —S(O)—$R_4$, —OS(O)—$R_4$, or —OS(O)O—$R_4$;
$R_4$ is

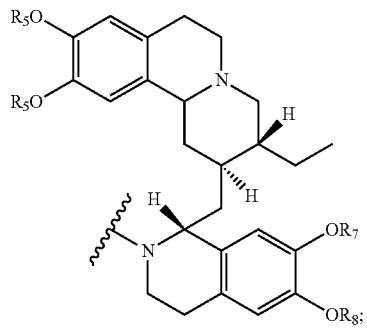

and
$R_5$, $R_6$, $R_7$ and $R_8$ are independently selected from the group consisting of H, $(C_1-C_6)$ alkyl, $(C_2-C_6)$ alkenyl, $(C_2-C_6)$ alkynyl, a Protecting Group and a Linker Unit.

2. The compound of claim 1 or a pharmaceutically acceptable salt thereof, wherein the compound has formula (Ia):

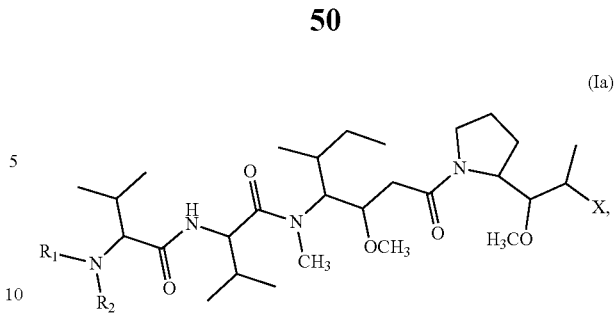

and $R_4$ is

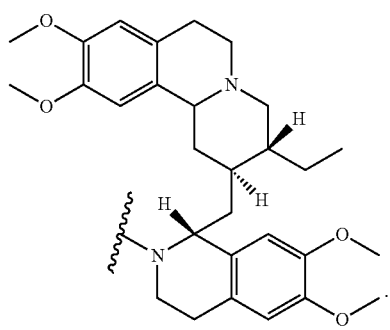

3. The compound of claim 1 or a pharmaceutically acceptable salt thereof, wherein the compound has formula (Ib):

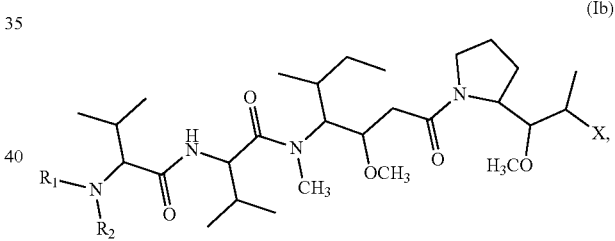

X is —C(O)$R_4$, —C(O)NH—$(C_{1-6}$ alkyl)-C(=O)—$R_4$, or —C(O)NH—$(C_{1-6}$ alkyl)-$R_4$; and
$R_4$ is

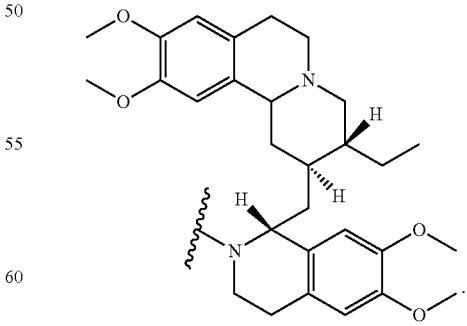

4. The compound of claim 1, wherein $R_1$ is H, $(C_1-C_6)$ alkyl, or a Linker Unit.
5. The compound of claim 1, wherein $R_1$ is H.
6. The compound of claim 1, wherein $R_1$ is methyl.

7. The compound of claim 1, wherein $R_1$ is a Linker Unit.

8. The compound of claim 1, wherein $R_2$ is H or ($C_1$-$C_6$) alkyl.

9. The compound of claim 1, wherein $R_2$ is H.

10. The compound of claim 1, wherein $R_2$ is methyl.

11. The compound of claim 1, wherein X is —C(O)$R_4$, —($C_{1-6}$ alkyl)-$R_4$, —($C_{1-6}$ alkyl)S(O)—$R_4$, —($C_{1-6}$ alkyl)-OS(O)—$R_4$, —($C_{1-6}$ alkyl)-OS(O)O—$R_4$, —S(O)—$R_4$, —OS(O)—$R_4$, or —OS(O)O—$R_4$.

12. The compound of claim 1, wherein X is —C(O)$R_4$.

13. The compound of claim 1, wherein $R_5$, $R_6$, $R_7$ and $R_8$ are independently H or ($C_1$-$C_6$) alkyl.

14. The compound of claim 11, wherein the Linker Unit comprises a glycosidic bond, a hydrazone, a cathepsin-B-cleavable peptide, a disulfide or an ester bond.

15. The compound of claim 1, wherein the Linker Unit has formula:

$A_a W_w Y_y$, wherein $A_a$ is maleimidocaproyl, $W_w$ is Valine-Citrulline and $Y_y$ is p-aminobenzyloxycarbonyl.

16. A compound selected from the group consisting of:

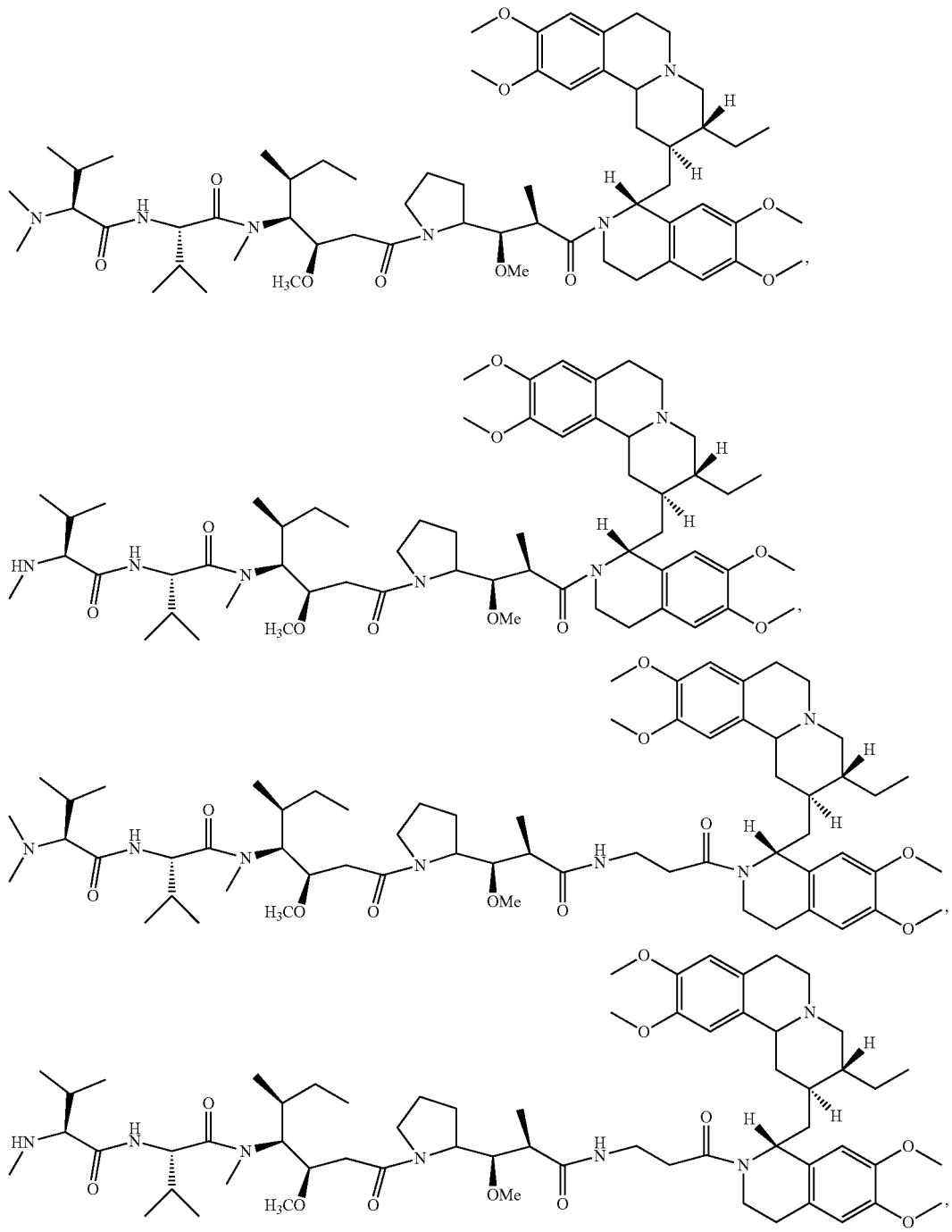

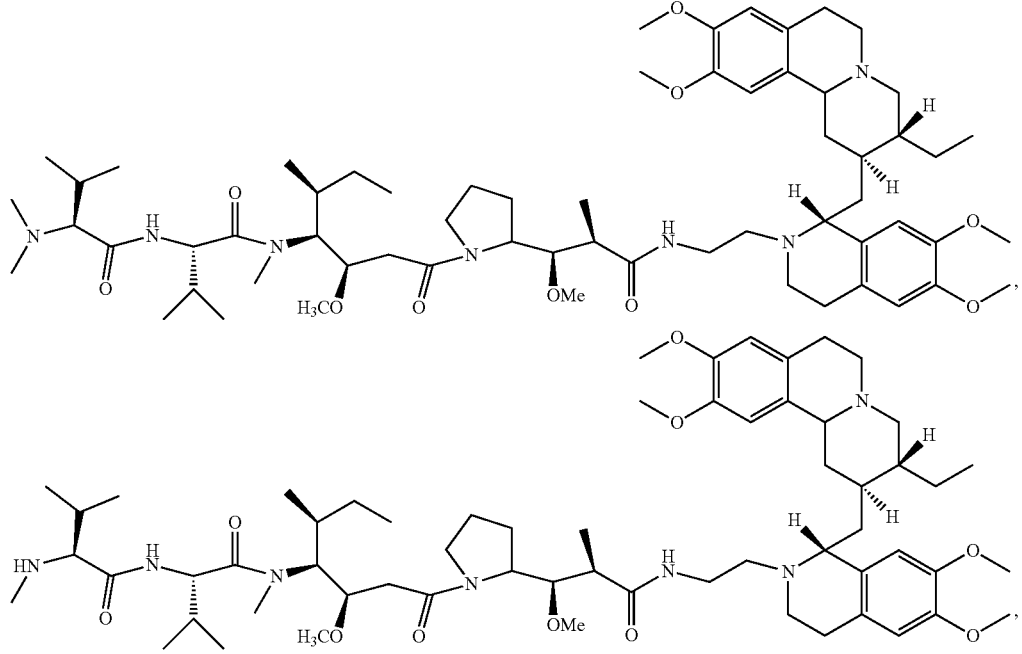

and pharmaceutically acceptable salts thereof.

17. A pharmaceutical composition comprising a compound of claim 1 or pharmaceutically acceptable salt thereof and a pharmaceutically acceptable carrier.

18. A method for killing or inhibiting the proliferation of tumor cells or cancer cells comprising treating the tumor cells or cancer cells with a compound of claim 1, or a pharmaceutical composition of claim 17 in an amount effective to kill or inhibit the proliferation of the tumor cells or cancer cells.

19. A method for treating cancer in a patient in need thereof comprising administering to the patient a compound of claim 1, or a pharmaceutical composition of claim 17, wherein the compound or pharmaceutical composition is administered in an amount effective to treat cancer, wherein the cancer is at least one selected from the group consisting of pancreas, breast, CNS, lung, colon, or prostate cancer.

20. A method of determining inhibition of cellular proliferation by a compound, comprising contacting cells in a cell culture medium with the compound of claim 1 and measuring the cytotoxic activity of the compound, whereby proliferation of the cells is inhibited.

21. A method of inhibiting the growth of tumor cells that overexpress a tumor-associated antigen comprising administering to a patient the compound of claim 1 conjugated to an antibody that is specific for said tumor-associated antigen, and optionally a second therapeutic agent wherein the compound and the second therapeutic agent are each administered in amounts effective to inhibit the growth of tumor cells in the patient.

22. An article of manufacture comprising the compound of claim 1, a container, and a package insert or label indicating that the compound can be used to treat cancer characterized by the overexpression of at least one tumor-associated antigen.

* * * * *